United States Patent
Lai et al.

(10) Patent No.: US 11,661,609 B2
(45) Date of Patent: May 30, 2023

(54) METHODS OF IDENTIFYING, SELECTING, AND PRODUCING DISEASE RESISTANT CROPS

(71) Applicant: HUAZHONG AGRICULTURAL UNIVERSITY, Hubei (CN)

(72) Inventors: Zhibing Lai, Hubei (CN); Hongze Wang, Hubei (CN); Jiabao Hou, Hubei (CN)

(73) Assignee: HUAZHONG AGRICULTURAL UNIVERSITY, Wuhan (CN)

( * ) Notice: Subject to any disclaimer, the term of this patent is extended or adjusted under 35 U.S.C. 154(b) by 0 days.

(21) Appl. No.: 17/147,105

(22) Filed: Jan. 12, 2021

(65) Prior Publication Data

US 2021/0214743 A1    Jul. 15, 2021

(30) Foreign Application Priority Data

Oct. 30, 2020 (CN) .......................... 202011200759.6

(51) Int. Cl.
  *C12N 15/82* (2006.01)
  *A01H 6/46* (2018.01)
(52) U.S. Cl.
  CPC ....... *C12N 15/8282* (2013.01); *A01H 6/4684* (2018.05)
(58) Field of Classification Search
  CPC .......................... C12N 15/8282; A01H 6/4684
  See application file for complete search history.

(56) References Cited

FOREIGN PATENT DOCUMENTS

| WO | WO 2010/083178 | 7/2010 |
| WO | WO 2013/098819 | 7/2013 |
| WO | WO 2019/236257 | 12/2019 |

OTHER PUBLICATIONS

Sequence Matches (Year: 2013).*
Xiuping Wang et al: Gene expression profiles in maize (L.) leaves inoculation with southern corn rust (Underw.), Acta Physiologiae Plantarum, Springer-Verlag, Berlin/Heidelberg, vol. 34, No. 3, Nov. 24, 2011 (Nov. 24, 2011), pp. 997-1006.
Chunjiang Zhou et al. Characterization and fine mapping of RppQ, a resistance gene to southern corn rust in maize , Molecular Genetics and Genomics, Springer, Berlin, DE, vol. 278, No. 6, Oct. 17, 2007 (Oct. 17, 2007), pp. 723-728.
Ya Zhang et al, Mapping of southern corn rust-resistant genes in the W2D inbred line of maize (Zea mays L.) 11 , Molecular Breeding, Kluwer Academic Pub Li Shers, DO, vol. 25, No. 3, Oct. 8, 2009 (Oct. 8, 2009), pp. 433-439.
CN 106,282,394 A (China Golden Marker (Beijing) Biotech Col. TD{ Jan. 4, 2017 (Jan. 4, 2017) Especiaiiy Abstract; p. 2, para 5; p. 5, para 1-2; p. 15, para 10.
AC234-75, Gen Bank Accession No. AC234175, Zea mays cultivar 873 chromosome 10 clone CH201-352E9, *** Sequencing in Progress•••, 22 unordered pieces, Sep. 13, 2014 (Online). [Retrieved on Jul. 7, 2020). f-1etrieved from the internet: <Uf-1L: 11ttps://v1,ww.ncbi.nlm.nih.gov/nuccore/AC234175>).
AC198651, Gen Bank Accession No. AC198651, Zea mays cultivar 873 chromosome 10 clone CH201-45H19, ' Sequencing in Progress*, 11 unordered pieces, Sep. 23, 2013 [online]. [Retrieved on Jul. 7, 2020). f-1etrieved from the internet: <Uf-1L: 11ttps://wNw.ncbi.nlm.nih.gov/nuccore/AC 198651 >).
PCT Search Report and Written Opinion prepared for PCT/US2019/032497, completed Jul. 16, 2019.
C. X. Chen et al, "Molecular tagging and genetic mapping of the disease resistance gene RppQ to southern corn rust", Theoretical and Applied Genetics; International Journal of Plant Breeding Research, 1/ol. 108, No. 5, Nov. 18, 2003 (Nov. 18, 2003), p. 945-950.
Wu Xiaojun et al, "Geographic and genetic identification of RppS, a novel locus conferring broad resistance to southern corn rust disease in China", Jan. 30, 2015 (Jan. 30, 2015), vol. 205, No. 1, p. 17-23.

* cited by examiner

*Primary Examiner* — Charles Logsdon
*Assistant Examiner* — Wayne Zhong
(74) *Attorney, Agent, or Firm* — Barnes & Thornburg LLP

(57) ABSTRACT

The present disclosure is related to plant breeding and methods of identifying and selecting plants with disease resistance. Provided are methods to identify novel genes that encode proteins providing plant disease resistance and uses thereof. These disease resistant genes are useful in the production of resistant plants through breeding, transgenic modification, or genome editing.

14 Claims, 1 Drawing Sheet

Specification includes a Sequence Listing.

SEQUENCE LISTING

```
<160> NUMBER OF SEQ ID NOS: 28

<210> SEQ ID NO 1
<211> LENGTH: 369
<212> TYPE: PRT
<213> ORGANISM: Zea Mays

<400> SEQUENCE: 1

Met Gly Leu Asp Val Met Glu Ile Gly Met Gly Ala Asp Leu Ser Leu
1               5                   10                  15

Asp Leu Arg His Phe Ala Ser Lys Ala Val Arg Gln Ser Lys Asp Asp
            20                  25                  30

Thr Pro Ala Pro Asp Met Asp Ala Cys Ile Arg Arg Leu Glu Glu Glu
        35                  40                  45

Arg Gly Lys Ile Glu Met Phe Lys Arg Asp Leu Pro Leu Cys Ala Arg
    50                  55                  60

Leu Leu Ala Asp Val Ile Asp Val Met Lys Glu Glu Ala Gly Lys Lys
65                  70                  75                  80

Lys Thr Thr Thr Arg Arg Arg Ser Asp Arg Arg Leu Ala Ser Ala Ala
                85                  90                  95

Ala Asp Asp Glu Glu Glu Glu Ala Asp Gly Ala Thr Ala Asp Lys Ser
            100                 105                 110

Lys Trp Met Ser Thr Ala Gln Leu Trp Thr Gly Asp Ser Gly Arg Glu
        115                 120                 125

Asp Ala Glu Ser Glu Lys Gln Asp Lys Gly Arg Cys Ser Pro Glu Ala
    130                 135                 140

Arg Ser Arg Gly Ala Leu Leu Pro Phe Lys Ala Asp Val Gly Ser Gly
145                 150                 155                 160

Ala Pro Ala Phe Ala Pro Leu Phe Leu Arg Thr Asp Asp Lys Ala Ala
                165                 170                 175

Ala Ala Arg Val Gly Val Pro Asp Leu Ser Ser Leu Leu Ser Pro Pro
            180                 185                 190

Ala Thr Met Pro Pro Ala Asp Ala Gly Ala Glu Glu Ser Arg Arg Gln
        195                 200                 205

Val Val Gly Phe Ala Gln Ala Ala Arg Ala Ala Ala Met Ala Pro
    210                 215                 220

Ser Ala Pro Ala Leu Gly Leu Gln Ser Gln Gln Gln Gln Gln Gln
225                 230                 235                 240

Gln Gln Ala Arg Lys Ala Arg Arg Cys Trp Ser Thr Glu Leu His Arg
                245                 250                 255
```

```
Lys Phe Val Ala Ala Leu Asp Gln Leu Gly Gly Pro Gln Val Ala Thr
                260                 265                 270

Pro Lys Gln Ile Arg Glu Leu Met Lys Val Asp Gly Leu Thr Asn Asp
            275                 280                 285

Glu Val Lys Ser His Leu Gln Lys Tyr Arg Leu His Asn Arg Arg Ala
        290                 295                 300

Pro Gly Ser Gly Val Val Arg Gln Pro Ile Val Leu Val Gly Gly Leu
305                 310                 315                 320

Trp Ile Pro Gln Glu Gln Gly Ser Pro Gln Ser Gly Ser Pro His Gly
                325                 330                 335

Pro Leu His His Leu Ser Thr Ser Val Ala Ala Val Ser Ala Ala
            340                 345                 350

Thr Ala Ser Cys Glu Glu Glu Asp Gly Arg Ser Glu Ser Tyr Gly Trp
        355                 360                 365

Lys

<210> SEQ ID NO 2
<211> LENGTH: 365
<212> TYPE: PRT
<213> ORGANISM: Zea Mays

<400> SEQUENCE: 2

Met Gly Leu Asp Val Met Glu Ile Gly Met Gly Ala Asp Leu Ser Leu
1               5                   10                  15

Asp Leu Arg His Phe Ala Ser Lys Ala Val Arg Gln Ser Lys Asp Asp
            20                  25                  30

Thr Pro Ala Pro Asp Met Asp Ala Cys Ile Arg Arg Leu Glu Glu Glu
        35                  40                  45

Arg Gly Lys Ile Glu Met Phe Lys Arg Asp Leu Pro Leu Cys Ala Arg
    50                  55                  60

Leu Leu Ala Asp Val Ile Asp Val Met Lys Glu Glu Ala Gly Lys Lys
65                  70                  75                  80

Lys Thr Thr Thr Arg Arg Ser Asp Arg Arg Leu Ala Ser Ala Ala Ala
                85                  90                  95

Asp Glu Glu Glu Glu Glu Asp Gly Ala Thr Ala Asp Lys Ser Lys
            100                 105                 110

Trp Met Ser Thr Ala Gln Leu Trp Thr Gly Asp Ser Gly Arg Glu Asp
        115                 120                 125

Ala Glu Ser Glu Lys Gln Asp Lys Gly Trp Cys Ser Pro Glu Ala Arg
    130                 135                 140

Ser Arg Gly Ala Leu Leu Pro Phe Lys Ala Glu Val Gly Ser Gly Ala
145                 150                 155                 160

Pro Ala Phe Ala Pro Leu Cys Leu Arg Thr Asp Lys Ala Ala Ala
                165                 170                 175

Ala Arg Val Gly Val Pro Asp Leu Ser Ser Leu Leu Ser Ser Pro Ala
            180                 185                 190

Thr Met Pro Pro Ala Asp Ala Gly Ala Glu Glu Ser Arg Arg Gln Val
        195                 200                 205

Val Gly Phe Ala Gln Ala Ala Arg Ala Ala Met Ala Pro Ser
    210                 215                 220

Ala Pro Ala Leu Gly Leu Gln Ser Gln Gln Gln Gln Gln Ala Arg
225                 230                 235                 240

Lys Ala Arg Arg Cys Trp Ser Thr Glu Leu His Arg Lys Phe Val Ala
                245                 250                 255
```

```
Ala Leu Asp Gln Leu Gly Gly Pro Gln Val Ala Thr Pro Lys Gln Ile
            260                 265                 270

Arg Glu Leu Met Lys Val Asp Gly Leu Thr Asn Asp Glu Val Lys Ser
        275                 280                 285

His Leu Gln Lys Tyr Arg Leu His Asn Arg Arg Ala Pro Gly Ser Gly
        290                 295                 300

Val Val Arg Gln Pro Ile Val Leu Val Gly Gly Leu Trp Ile Pro Gln
305                 310                 315                 320

Glu Gln Gly Ser Pro Gln Ser Gly Ser Pro His Gly Pro Leu His His
                325                 330                 335

Leu Ser Thr Ser Val Ala Ala Val Ser Ser Ala Ala Thr Ala Ser Cys
            340                 345                 350

Glu Glu Glu Asp Gly Arg Ser Glu Ser Tyr Gly Trp Gln
        355                 360                 365

<210> SEQ ID NO 3
<211> LENGTH: 367
<212> TYPE: PRT
<213> ORGANISM: Zea Mays

<400> SEQUENCE: 3

Met Gly Leu Asp Val Met Glu Ile Gly Met Gly Ala Asp Leu Ser Leu
1               5                   10                  15

Asp Leu Arg His Phe Ala Ser Lys Ala Val Arg Gln Ser Lys Asp Asp
            20                  25                  30

Thr Pro Ala Pro Asp Met Asp Ala Cys Ile Arg Arg Leu Glu Glu Glu
        35                  40                  45

Arg Gly Lys Ile Glu Met Phe Lys Arg Asp Leu Pro Leu Cys Ala Arg
    50                  55                  60

Leu Leu Ala Asp Val Ile Asp Val Met Lys Glu Glu Ala Gly Lys Lys
65                  70                  75                  80

Thr Thr Thr Thr Arg Arg Ser Asp Arg Arg Leu Ala Ser Ala Ala Ala
                85                  90                  95

Asp Glu Glu Glu Glu Glu Asp Gly Ala Thr Ala Asp Lys Ser Lys
            100                 105                 110

Trp Met Ser Thr Ala Gln Leu Trp Thr Gly Asp Ser Gly Arg Glu Asp
        115                 120                 125

Ala Glu Ser Glu Lys Gln Asp Lys Gly Arg Cys Ser Pro Glu Ala Arg
    130                 135                 140

Ser Arg Gly Ala Leu Leu Arg Phe Lys Ala Asp Val Gly Ser Gly Ala
145                 150                 155                 160

Pro Ala Phe Ala Pro Leu Cys Leu Arg Thr Asp Lys Ala Ala Ala
                165                 170                 175

Ala Arg Val Gly Val Pro Asp Leu Ser Ser Leu Leu Ser Pro Pro Ala
            180                 185                 190

Thr Met Pro Pro Ala Asp Ala Gly Ala Glu Glu Ser Arg Arg Gln Val
        195                 200                 205

Val Gly Phe Ala Gln Ala Ala Arg Ala Ala Met Ala Pro Ser
    210                 215                 220

Ala His Ala Leu Gly His Gln Ser Gln Ser Gln Gln Gln Gln Gln
225                 230                 235                 240

Ala Arg Lys Ala Arg Arg Cys Trp Ser Thr Glu Leu His Arg Lys Phe
                245                 250                 255
```

```
Val Ala Ala Leu Asp Gln Leu Gly Gly Pro Gln Val Ala Thr Pro Lys
            260                 265                 270
Gln Ile Arg Glu Leu Met Lys Val Asp Gly Leu Thr Asn Asp Glu Val
        275                 280                 285
Lys Ser His Leu Gln Lys Tyr Arg Leu His Asn Arg Arg Ala Pro Gly
    290                 295                 300
Ser Gly Val Val Arg Gln Pro Ile Val Leu Val Gly Gly Leu Trp Ile
305                 310                 315                 320
Pro Gln Glu Gln Gly Ser Pro Gln Ser Gly Ser Pro His Gly Pro Leu
                325                 330                 335
His His Leu Ser Thr Ser Val Ala Ala Val Ser Ala Ala Thr Ala
            340                 345                 350
Ser Cys Glu Glu Glu Asp Gly Arg Ser Glu Ser Tyr Gly Trp Lys
        355                 360                 365

<210> SEQ ID NO 4
<211> LENGTH: 5006
<212> TYPE: DNA
<213> ORGANISM: Zea Mays

<400> SEQUENCE: 4
cgttcacgcg attttcaag tgaaagcgag accgaaaacc agcaatgggc tgtaggaatg      60
cattaggata tttttaccaa atattagcca acgtttttg ttattatgca ataatagtagg    120
catagcacta aatttacaat agactacaaa tatagggct ttattacaaa atattctttc     180
ggacgtgaaa actcgtcatt gttgattcgg agattctacc actccatctc cagttttttc    240
cctcgcctgc tcagctcccc tataaatgga gctcgccttc cgcggcctcc ctccgttccc    300
atccgccgcc cgcgcacttc ttccttcggg cacacaggac accaccgtcg acggattcat    360
cgcgacgatg gggctcgacg tcatggagat cgggatgggc gccgatttga gcctggatct    420
gaggcacttc gcctccaagg ccgtgaggca gagcaaggac gacacgccgg cgccggacat    480
ggacgcatgc atccgccgcc tcgaggagga gcggggtaag atcgagatgt tcaagcggga    540
cctcccgctc tgcgcgcgcc tcctcgccga cggtgagcgc acctacctct tctcctctct    600
ctctgtctct ctctctttt atttttccca cctgtgattc atttgggata ccttttgctt    660
cttttccattt tggggagcgg ttttttttac gcggcgatgc ggtggcgtgt gcgcagtaat    720
tgatgtcatg aaggaggagg cggggaagaa gaagacgacg acaaggagga gtgaccgcag    780
gctggcgtct gcggcagctg atgaggagga ggaggaggag gacggcgcca ccgcggacaa    840
gagcaagtgg atgagcacgg cgcagctctg gacgggcgat ccgggcggg aggacgcgga    900
atcagaggta cggcacgatt cgatcgctgg tgcagctgct tgaatgctca gtcagcacag    960
gatctggagg gtgctgtcgg gtgctcgatt cgtcggcagg cctaaaagtt tggagctttg    1020
cgatcgcaga agcaagacaa ggggtggtgc tcgccggagg ccaggtcccg cggcgctctc   1080
ttaccgttca aggctgaagt gggctctggc gcgccggcgt tcgcgccgct ctgcttgaga   1140
acggacgaca aggctgcggc tgcgcgcgtc ggggtgccgg atctgtcgtc cttgctgtcg   1200
tcgccggcga ccatgcctcc tgcggacgcc ggcgccgagg agagccgtcg ccaggttgtg   1260
ggatttgcgc aagctgcggc cagggcggct gccatggcgc cgtctgcccc tgcgcttggg   1320
ctccagtcgc agcagcagca gcagcaggca aggaaggctc ggcgttgctg gtcgacggag   1380
ctgcatcgca agttcgtcgc cgccttggat cagctcggtg gccccaagg tgagccttgc    1440
cttgttcttc ggatgccagt tcaccagaat ctcttgccag ttttgagcca ccaacacgtt   1500
```

```
caatcttacc tagttgctag ctgccttcca tattagaatc ataaaattgg gatcaatgag    1560
tctatgccat gactgcagtt gccacgccga agcaaatcag ggagctgatg aaggtggatg    1620
ggctgacaaa cgacgaagtg aaaagccatc ttcaggttag cgatccagca gcagctcact    1680 cccccttgcca ttccattcat ccatctcatc tcaggaagtc acgagtatct gttgttgtga    1740
tggttgctga atggattct ccgatttcga tgtctcttca gaaataccgg ctgcacaacc     1800
ggagggcgcc tggatccggc gtggtgcgcc agccgatcgt gctcgtggga gggctgtgga    1860
ttccccagga gcaaggcagc cctcagtctg gatctcccca cggcccctc caccacctgt     1920 ccacctcggt ggccgccgtc tcgtccgccg ccaccgccag ctgcgaggag gaagacggcc    1980
ggtccgagag ctatggctgg caatgatgtc tggctgctgc tgctgctgca ccaccaatgt    2040
gtgttcactg ttcagagagg ggaggtttct tggcatggtg gggatcgcca tgggccatgg    2100
cggaggccac cagttgcagc ttcaggaatc gggaggggaa ttgagtgtag tgtagctgtc    2160
tgtacacata catacataca tacagtgaga tgggatgaga tgagagcggg ccttgagcgc    2220
tcgagatcag aactgatggt gcttcgtcgt cgggtttgta catcccaaag agaaagagat    2280
actagctaca gttttgcggc ttgttaatcc atgctctggg ggcagagcta cagttttcgc    2340
cccgagagag ttcacccata cccgttgttg tcgattagac gattaccatc ttcgccttct    2400
tgttgccgtt gaacaaaatg ttgcttccgc tgttcgtctc ggaacgaaca gtccggttga    2460
aaagttgaat cgttgcagga gtacatgcta ctcaggctgt aatgtggttg gtaagggtgt    2520
ttgaatgaac tagacctaat agttagtgac taaaattagt tggatacatc taaacatcct    2580
ataatcctat agtttaacta ttagatattt gttatctcgc taattttata agtaattttt    2640
agccaactaa ctattagttc taatgcattc gaacgctcac tctgcagctt ccagtcgcg    2700 tatcgttcag gtctatctaa ctgaaagagc agcaaagaag aaagagatct caataagaaa    2760
agaacccgat tccaccattg aacaaccaac caagagggtt gctcctgctc ctctgctgtt    2820
caccatcatc aacagcacgt aaaaaaaatc tctagctctc tactttaccg tctaccagta    2880
gtgtttggat aaagcaacag aagccggctt ctcttctttt tttgcagaga taatatagat    2940
attcagaaga agaaaaaaga attatctggg cctaactgaa actgagctga cggagcacga    3000
gcacggaagc catgcttgtt gtatacataa cataagccgg ggggaggata tgctcgaggc    3060
attctcttct tcctcctccg tcagtcactg gtccggtcca ttcgttagcg tctcaccagt    3120
ccttgatcag cattgttaat actactagct cgctgctgag tgctgacaat gcgaaacagt    3180
ttcttggcag gattccaact cgagctcgcc gtcgctgtcg ctgtcgctgg accgtaggaa    3240
cgtgccggtc ccctccctgc atggcgggcc aaagagccac ccagatcaga ggacggatcc    3300
ccgtgaaatc ccccctcttg ttctttaatt actcgcaggc ggaggaaagg cggcagtgca    3360
cagcgacaga gagacgaaga ctttggaatc gtccttgggt ggatggatgg acggacgaac    3420
gaggcggggc cgcgagctct gaatattcgc cgccgtcgat gcatcggcgg cctgcctgtc    3480
gctgtcgacg gagagggtgg tactggtgtg cgcaaccgga caacgcaatg ttcaggcctg    3540
aagaatcgga atcggaatat tatattccgt ctggtgtggt tgtcactttc ttttctttgt    3600
gtgtgttttt ttgttgtttg ttgttgttgt gtagataaat actatgggga agaatggagg    3660
gggatatgag gatatcctcg ttgattctgc ttgagaaact agggcgtatt atatgataca    3720
tacatttgga attctcactc tcggccgacc ccgccggcga cctcagcccg acgtggatat    3780
ataaaaaaaa agatgattaa agctttgtaa gataagacta gtctgcactt tctagtagat    3840
```

```
ttagaccata ttttgaaacg tctgaaacta ataattaaca gataaaacta gctaagagag      3900
aacgaatcag ctaatagatt agctaattgc tggttacatc tctcaaatag ctattagtta      3960
ttagttaatt taatctagct aaaatcaaat acaacaactt actctttatg tacaaaatta      4020
aaatttgttt tagtttttta ttggattcat ataataattt gtgttatgt ttttttatat      4080 gtttctaaat ttattatata aaaactaaga gataaaatga ataataattt ttggacggaa      4140
agaatattag ctccctacag ttttgggaca ggtcgcaact tgtctgacta gttaagtttc      4200
tatagcgcgg tagtagtcta gtagaagata gtactctctt tgtttctttt tagttattat      4260
tggataattt aattttgtaa tattcagcga caactaaaac gaaacgtaag agagggtaga      4320
taactttgga gacttgagtc gtcgtgaatg ggatgggact tgtcggagcc tcggcgcagc      4380
gtattatttg ttgacagggc cgtgagagcc tggtccacat tttgttggcc catttaggtg      4440
agctgtctac agattgggcc gagcaagtaa gggtatagga agccgaaatg tgcccattta      4500
accaatcatc acggtttgag tcgacattcc acgattctgc aaccacagta ctttatttat      4560
ttggttgaaa acacaaggtt aattaatact aacagtagcg acaatgatga tgctccttca      4620
cgcttccttg ccatatcata aaaaaacagt aaaaaggtaa agaaaaagg ttaatgccta      4680 cctatagctt ttagcttgca gcgcgccctc tctctcttct ctctgtatat atgccgtgat      4740
cgccggcaca catcgcggcg tgtttgcatt ccgatcggcg gccgcgaaaa aggaaaaata      4800
aagaagtgaa aaatagagga aagcagaaag aataaaagag ggctaaaaga aaaaggcatg      4860
tcgccgtatg ctggcgcctt gatagtcagg ggctcagggc gtcaggcaga catgcttgta      4920
gtagttagta tatagagtcc ggccgacacg gttcagcggc cacatgcatg cagcgacagg      4980
ctaatcaaag cccacaacag agaccg                                          5006

<210> SEQ ID NO 5
<211> LENGTH: 5256
<212> TYPE: DNA
<213> ORGANISM: Zea Mays

<400> SEQUENCE: 5
cgttcacgcg attttcaag tgaaagccaa atattagcca aacgtttttg ttattatgca       60
taatagtagg catagcacta aatttacaat agactacaaa tatagggct ttcgtacaaa      120 ataatctttc ggacgtgaaa actcgtcatt gttgattcgg agattctacc actccatctc      180
cagttttttt ttccctcgcc tgctcggctc ccctataaat ggagctcacc ttccgcggcc      240
tccctccgtt cccatccgcc gcccgcgcac ttcttccttc gggcacacag gacaccaccg      300
tcgacggatt catcgcgacg atggggctcg acgtcatgga gatcgggatg ggcgccgatt      360
tgagcctgga tctgaggcac ttcgcctcca aggccgtgag gcagagcaag gacgacacgc      420
cggcgccgga catggacgca tgcatccgcc gcctcgagga ggagcggggt aagatcgaga      480
tgttcaagcg ggacctcccg ctctgcgcgc gcctcctcgc cgacggtgag cgcacctacc      540
tcttctctct ctgtctctct ctctttttta tttttcccac ctgtgattca tttgggatac      600
cttctgcttc tttccatttt ggggagcggg tttttttatg cggcgatgtg gtggcgtgtg      660
cgcagtaatt gatgtcatga aggaggaggc gggaagaag acgacgacca cgaggaggag      720
tgatcgcagg ctggcgtctg cggcagctga tgaggaggag gaggaggagg acggcgccac      780
cgcggacaag agcaagtgga tgagcacggc gcagctctgg acgggcgatt ccggcgggga      840
ggacgcggaa tcagaggtac ggcacgattc gatcgctggt gcagctgctt gaatgcccag      900
tcagcacagg atctgggggg tgctgtcggg tgctcgattc gtcggcaggc ctaaaagttt      960
```

```
tggagctttg cgatcgcaga agcaagacaa ggggcggtgc tcgccggagg ccaggtcccg    1020
cggcgctctc ttacggttca aggctgatgt gggctctggc gcgccggcgt tcgcgccgct    1080
ctgcttgaga acggacgaca aggctgcggc tgcgcgcgtc ggggtgccgg atctgtcgtc    1140
cttgctgtcg ccgccggcga ccatgcctcc tgccgacgcc ggcgccgagg agagccgtcg    1200
ccaggttgtg ggatttgcgc aagctgcggc cagggcggct gccatggcgc cgtctgccca    1260
tgcgcttggg caccagtcgc agtcgcagca gcagcagcag caggcaagga aggctcggcg    1320
ttgctggtcg acggagctgc atcgcaagtt cgtcgccgcc ttggatcagc tcggtggccc    1380
ccaaggtgag ccttgccttg ttcttcggat gccagttcac cagaatttct tgccagtttt    1440
gggccaccaa cacacacgtt caatcttacc tagttgctag ctgccttcca tattatatta    1500
gaaacactga gttcattcat gctacgccat gcctgcagtt gccacgccga agcaaatcag    1560
ggagctgatg aaggtggatg ggctgacaaa cgacgaagtg aaaagccatc ttcaggttag    1620
cgatccagca gcagctcact ccccttgaca ttccattcat ccatctcatc tcaggaagtc    1680
acgaatatct gttgttgtga tggttgctga aatggattct ctgatttcga tgtttgttca    1740
gaaataccgg ctgcacaacc gcagggcgcc tggatccggc gtggtgcgcc agccgatcgt    1800
gctcgtggga gggctgtgga ttccccagga gcaaggcagc cctcagtctg gatctcccca    1860
cggccctctc caccacttgt ccacctcggt ggccgccgtc tcgtccgccg ccaccgccag    1920
ctgcgaggag gaagacggcc ggtccgagag ctatggctgg aaatgatgaa gaggctgctg    1980
ctgctgctgc accaccaatg tgtgttcact gtttagagag gggaggtttc ttggcatggt    2040
ggggatcgcc atgggccatg gcggaggcca ccagttgcag cttcaggaat cgggagggga    2100
attgagtgta gtgtagctgt ctgtacacat acatacatac atacattgag atgggatgag    2160
atgagagcgg gccttgagcg ctcgagatca gaactgatgg tgcttcgtcg tcgggtttgt    2220
acatcccaaa gagaaagaga aagagatact agctacagtt ttgcggcttg ctaatccatg    2280
cctgggggca gagctacagt tttcgccccg agagagttca cccatcaccc ataccgttg     2340 ttgtcgatta ccatcttcgc cttcttgttg ccgttgaaca aaatgttgct ttcgctgttc    2400
gtctcggaac gaacagtccg gttgaaaagt tgaatcgttg caggagtaca tgctactgag    2460
tctgtaatgt ggttggtaag ggtgtttgaa tgaactagac ctaatagtta gtgactaaaa    2520
ttagaatcat atagtttaac tattagatat ttgttatctc gctaatttta taagtaattt    2580
ttagccaact aactattagt tcgaatgcat tcgaacactc actctgcagc tttccagtcg    2640
cgtatcgtta aggtctatct aactgaaaga gcagcaaaga tgaaagagat ctcaataaga    2700
aaagaacccg attccaccat tgaacaacca accaagaggg ttgctcctgc tcctctgctg    2760
ttcaccatca tcaacagcac gtaaaaaaaa aatctctagc tctctactgt accgtctacc    2820
agtagtgttt ggataaagca acagacgccg gtttctcttc tttttttacag ataatata     2880 gatattcaga agaagaagaa aaaggaataa ttatctgggc ctaactgaaa ctgagctgac    2940
ggagcacgag cacggaagcc atgcttgttg tatacataac ataagccggg gggaggatat    3000
gctcgaggca ttctcttctt cctcatccgt cagtcactgg ctcggtccat tcgttagcgt    3060
ctcaccagtc cttgatcagc attgttaata ctactagctc gctgctgagt gctgactatg    3120
cgaaacagtt tcttggcagg attccaacaa ctcgagctcg ccgtcgccgt cgctgtcgct    3180
ggaccgtacg aacgtgccgg tccctcccct gcatggcgga ccaaagagcc acccagatca    3240
ggacggatcc ccgtgaaatc cccctcttg ttctttaatt actcgcaggc ggaggaaagg      3300
```

| | |
|---|---|
| cggcagtgca cagcgacaga gagacgaaga ctttggaatc gtccttgggt gcatggatgg | 3360 |
| acggacggac gaacgagagg gggggccgcg agctctgaat attcgccgcc gtcgatgcat | 3420 |
| cggcggcctg cctgtcgctc tcgacggaga gggtggtact ggtgtgcgca accggacaac | 3480 |
| gcaatgttca ggccgaagaa atcggaatcg gaatatcata ttccgtctgg tgtggtggtc | 3540 |
| actttctttt ctttgtgtgt gtgttttttt gttgttgttg tgtagataaa tactatgggg | 3600 |
| aagaatggag gggatatgag gatatcctcg ttgattctgc ttgagaaact agggcgtatt | 3660 |
| atatgataca tttggaattc tcactctcgg ctgggccgac cccgccggcg acctcagccc | 3720 |
| gacgtggata tatataaaaa gatgattaaa gctttgtaag ataagactag tctgcacttt | 3780 |
| ctagtagatt tagaccatat tttcaaacgt ctaaaactaa taatgaacag ataaaactag | 3840 |
| ctaagagaga acgaatcagc taatagatta gctaattgtt agttacattt ctcaaatagc | 3900 |
| tattagttgt tagttaattt aatctagcta aaatcaacta caacaactta ctctttatgt | 3960 |
| acaaaattaa aatttgtttt agttttttat tggattcata taataatttg tgtttatgtt | 4020 |
| ttttatatg tttctaaatt tattatataa aaactaagag ataaaatgaa taataatttt | 4080 |
| tggacggaaa gaatattagc tccctacagt tttgggacag gtcgcaactt gtctgactag | 4140 |
| ttaagtttct atagcgcggt agtagtctag tagaagatag tactctcttt gtttcttttt | 4200 |
| agttattatt ggataattta attttgtaat attcagcgac aactaaaacg aaacgtaaga | 4260 |
| gagggtagat aactttggag acttgagtcg tcgtgaatgg gatgggactt gtcggagcct | 4320 |
| cggcgcagcg tattatttgt tgacagggcc gtgagagcct ggtccacatt ttgttggccc | 4380 |
| atttaggtga gctgtctaca gattgggccg agcaagtaag ggtataggaa gccgaaatgt | 4440 |
| gcccatttaa ccaatcatca cggtttgagt cgacattcca cgattctgca accacagtac | 4500 |
| tttatttatt tggttgaaaa cacaaggtta attaatacta acagtagcga caatgatgat | 4560 |
| gctccttcac gcttccttgc catatcataa aaaacagtaa aaaggtaaaa gaaaaaggtt | 4620 |
| aatgcctacc tatagcttgc agcgcgccct ctctctcttc tctctgtata tatgccgtga | 4680 |
| tcgccggcac acatcgcggc gtgtttccat tccgatcggc ggcggcgaaa aagggaaaaa | 4740 |
| taaagaagta aaaatagag gaaagcagaa agaaaaaaaa aagggttaaa agaaaaggca | 4800 |
| tgtcgccgta tgctggcgcc ttgatagtca ggcagacatg ctttgcagta gtagtagtat | 4860 |
| ataggggtgtg tttggtttga cttttgactc tggcttttac cccctaaaag ctaaaagcca | 4920 |
| aaccaaaggg ctggatttag gaagcagctt tttctaaaag ccgactttct tgcagtgcaa | 4980 |
| aactgaaagc acctctagac ctgcttttag ctgcttttag atggaactgt gaaaatatat | 5040 |
| atggaaaaac atttagcgac ttttagtggt ttccaccaaa cacttttag ctttttaaca | 5100 |
| gctcgcagcc cacagcagct tttctcacag ctcacagccc acagcagctt ttttcacagc | 5160 |
| cacagtccaa ccaaacagac catagagtcc ggccgacacg gttcagcggc cacatgcatg | 5220 |
| cagcgacagt ctaatcaaag cccacaacag agaccg | 5256 |

<210> SEQ ID NO 6
<211> LENGTH: 2084
<212> TYPE: DNA
<213> ORGANISM: Zea Mays

<400> SEQUENCE: 6

| | |
|---|---|
| gttcccatcc gccgcccgcg cacttcttcc ttcgggcaca caggacacca ccgtcgacgg | 60 |
| attcatcgcg acgatggggc tcgacgtcat ggagatcggg atgggcgccg atttgagcct | 120 |
| ggatctgagg cacttcgcct ccaaggccgt gaggcagagc aaggacgaca cgccggcgcc | 180 |

-continued

```
ggacatggac gcatgcatcc gccgcctcga ggaggagcgg ggtaagatcg agatgttcaa      240
gcgggacctc ccgctctgcg cgcgcctcct cgccgacggt gagcgcacct acctcttctc      300
ctctcttctg tctctctctt ttttattttt cccacctgtg attcatttgg gataccttct      360
gcttctttcc attttgggga gcggtttttt ttatgcggcg atgcggtggc gtgtgcgcag      420
taattgatgt catgaaggag gaggcgggga agaagaagac gacgacgagg aggaggagtg      480
atcgcaggct ggcgtctgcg gcagctgatg atgaggagga ggaggcggac ggcgccaccg      540
cggacaagag caagtggatg agcacggcgc agctctggac gggcgattcc gggcgggagg      600
acgcggaatc agaggtacgg cacgattcga tcgctggtgc agctgcttga atgctcagtc      660
agcacaggat ctgtggggt gctgtcgggt gctcgattcg tcggtgggcc taaaagtttt       720
ggagctttgc gatcgcagaa gcaagacaag gggcggtgct cgccgaggc caggtcccgc       780 ggcgctctct taccgttcaa ggctgatgtg ggctctggcg cgccggcgtt cgcgccgctc      840
ttcttgagaa cggacgacaa ggctgcggct gcgcgcgtcg gggtgccgga tctgtcgtcc      900
ttgctgtcgc cgccggcgac catgcctcct gcggacgccg cgccgagga gagccgtcgc      960 caggttgtgg gatttgcgca agctgcggcc agggcggctg ccatgcgcc gtctgccct      1020 gcgcttgggc tccagtcgca gcagcagcag cagcagcagc agcaggcaag gaaggctcgg     1080
cgttgctggt cgacggagct gcatcgcaag ttcgtcgccg ccttggatca gctcggtggc     1140
ccccaaggtg agccttgcct tgttcttcgg atgccagttc accagaattt cttgccagtt     1200
ttgggccacc aacacacacg tccaatctta cctagttgct agctgccttc catattatat     1260
tagaaagaaa cattgagttc attcatgcta cgccatgcct gcagttgcca cgccgaagca     1320
aatcagggag ctgatgaagg tggatgggct gacaaacgac gaagtgaaaa gccatcttca     1380
ggttagcgat ccagcagcag ctcagtccac ttggcattcc attcatccat ctcaggaagt     1440
cacgaatatc tgttgttttg atggttgctg aaatggattc tctaattccg atgtttattc     1500
agaaataccg gctcacaac cgcagggcgc ctggatccgg cgtggtgcgc cagccgatcg     1560
tgctcgtggg agggctgtgg attccccagg agcaaggcag ccctcagtct ggatctcccc     1620 acggcccct ccaccacctg tccacctcgg tggccgccgt ctcgtccgcc gccaccgcca     1680
gctgcgagga ggaagacggc cggtccgaga gctatggctg gaaatgatga agaggctgct     1740
gctgctgctg ctgcgccacc aatgtgtgtt cactgtttag agaggggagg gaggtttctt     1800
ggcatggtgg ggatcgccat gggccatggc ggaggccacc agttgcagct tcaggaatcg     1860 ggagggggaat tgagtgtagt gtagctgtct gtacacatac atacatacat acagtgagat    1920
gggatgagat gagagcgggc cttgagcgct cgagatcaga actgatggtg cttcgtcgtc     1980
gggtttgtac atcccaaaga gaaagagata ctagctacag ttttgcggct tgttaatcca     2040
tgctctgggg gcagagctac agttttcgcc ccgagagagt tcac                      2084
```

<210> SEQ ID NO 7
<211> LENGTH: 1540
<212> TYPE: DNA
<213> ORGANISM: Zea Mays

<400> SEQUENCE: 7

```
gttcccatcc gccgcccgcg cacttcttcc ttcgggcaca caggacacca ccgtcgacgg       60
attcatcgcg acgatggggc tcgacgtcat ggagatcggg atgggcgccg atttgagcct      120
ggatctgagg cacttcgcct ccaaggccgt gaggcagagc aaggacgaca cgccggcgcc      180
```

-continued

| | |
|---|---|
| ggacatggac gcatgcatcc gccgcctcga ggaggagcgg ggtaagatcg agatgttcaa | 240 |
| gcgggacctc ccgctctgcg cgcgcctcct cgccgacgta attgatgtca tgaaggagga | 300 |
| ggcggggaag aagaagacga cgacgaggag gaggagtgat cgcaggctgg cgtctgcggc | 360 |
| agctgatgat gaggaggagg aggcggacgg cgccaccgcg gacaagagca agtggatgag | 420 |
| cacggcgcag ctctggacgg gcgattccgg gcgggaggac gcggaatcag agaagcaaga | 480 |
| caaggggcgt tgctcgccgg aggccaggtc ccgcggcgct ctcttaccgt tcaaggctga | 540 |
| tgtgggctct ggcgcgccgg cgttcgcgcc gctcttcttg agaacggacg acaaggctgc | 600 |
| ggctgcgcgc gtcggggtgc cggatctgtc gtccttgctg tcgccgccgg cgaccatgcc | 660 |
| tcctgcggac gccggcgccg aggagagccg tcgccaggtt gtgggatttg cgcaagctgc | 720 |
| ggccagggcg gctgccatgg cgccgtctgc ccctgcgctt gggctccagt cgcagcagca | 780 |
| gcagcagcag cagcagcagg caaggaaggc tcggcgttgc tggtcgacgg agctgcatcg | 840 |
| caagttcgtc gccgccttgg atcagctcgg tggcccccaa gttgccacgc cgaagcaaat | 900 |
| cagggagctg atgaaggtgg atgggctgac aaacgacgaa gtgaaaagcc atcttcagaa | 960 |
| ataccggctg cacaaccgca gggcgcctgg atccggcgtg gtgcgccagc cgatcgtgct | 1020 |
| cgtgggaggg ctgtggattc cccaggagca aggcagccct cagtctggat ctccccacgg | 1080 |
| cccccctccac cacctgtcca cctcggtggc cgccgtctcg tccgccgcca ccgccagctg | 1140 |
| cgaggaggaa gacggccggt ccgagagcta tggctggaaa tgatgaagag gctgctgctg | 1200 |
| ctgctgctgc gccaccaatg tgtgttcact gtttagagag gggagggagg tttcttggca | 1260 |
| tggtggggat cgccatgggc catggcggag gccaccagtt gcagcttcag gaatcgggag | 1320 |
| gggaattgag tgtagtgtag ctgtctgtac acatacatac atacatacag tgagatggga | 1380 |
| tgagatgaga gcgggccttg agcgctcgag atcagaactg atggtgcttc gtcgtcgggt | 1440 |
| ttgtacatcc caaagagaaa gagatactag ctacagtttt gcggcttgtt aatccatgct | 1500 |
| ctgggggcag agctacagtt ttcgccccga gagagttcac | 1540 |

<210> SEQ ID NO 8
<211> LENGTH: 1098
<212> TYPE: DNA
<213> ORGANISM: Zea Mays

<400> SEQUENCE: 8

| | |
|---|---|
| atggggctcg acgtcatgga gatcgggatg ggcgccgatt tgagcctgga tctgaggcac | 60 |
| ttcgcctcca aggccgtgag gcagagcaag gacgacacgc cggcgccgga catggacgca | 120 |
| tgcatccgcc gcctcgagga ggagcggggt aagatcgaga tgttcaagcg ggacctcccg | 180 |
| ctctgcgcgc gcctcctcgc cgacgtaatt gatgtcatga aggaggaggc ggggaagaag | 240 |
| aagacgacga caaggaggag tgaccgcagg ctggcgtctg cggcagctga tgaggaggag | 300 |
| gaggaggagg acggcgccac cgcggacaag agcaagtgga tgagcacggc gcagctctgg | 360 |
| acgggcgatt ccgggcggga ggacgcggaa tcagagaagc aagacaaggg gtggtgctcg | 420 |
| ccggaggcca ggtcccgcgg cgctctctta ccgttcaagg ctgaagtggg ctctggcgcg | 480 |
| ccggcgttcg cgccgctctg cttgagaacg gacgacaagg ctgcggctgc gcgcgtcggg | 540 |
| gtgccggatc tgtcgtcctt gctgtcgtcg ccggcgacca tgcctcctgc ggacgccggc | 600 |
| gccgaggaga gccgtcgcca ggttgtggga tttgcgcaag ctgcggccag gcggctgcc | 660 |
| atggcgccgt ctgcccctgc gcttgggctc agtcgcagc agcagcagca gcaggcaagg | 720 |
| aaggctcggc gttgctggtc gacggagctg catcgcaagt tcgtcgccgc cttggatcag | 780 |

```
ctcggtggcc cccaagttgc cacgccgaag caaatcaggg agctgatgaa ggtggatggg    840
ctgacaaacg acgaagtgaa aagccatctt cagaaatacc ggctgcacaa ccggagggcg    900
cctggatccg gcgtggtgcg ccagccgatc gtgctcgtgg gagggctgtg gattccccag    960
gagcaaggca gccctcagtc tggatctccc cacggccccc tccaccacct gtccacctcg   1020
gtggccgccg tctcgtccgc cgccaccgcc agctgcgagg aggaagacgg ccggtccgag   1080
agctatggct ggcaatga                                                 1098

<210> SEQ ID NO 9
<211> LENGTH: 1104
<212> TYPE: DNA
<213> ORGANISM: Zea Mays

<400> SEQUENCE: 9
atggggctcg acgtcatgga gatcgggatg ggcgccgatt tgagcctgga tctgaggcac     60
ttcgcctcca aggccgtgag gcagagcaag gacgacacgc cggcgccgga catggacgca    120
tgcatccgcc gcctcgagga ggagcggggt aagatcgaga tgttcaagcg ggacctcccg    180
ctctgcgcgc gcctcctcgc cgacgtaatt gatgtcatga aggaggaggc ggggaagaag    240
acgacgacca cgaggaggag tgatcgcagg ctggcgtctg cggcagctga tgaggaggag    300
gaggaggagg acggcgccac cgcggacaag agcaagtgga tgagcacggc gcagctctgg    360
acgggcgatt ccgggcggga ggacgcggaa tcagagaagc aagacaaggg gcggtgctcg    420
ccggaggcca ggtcccgcgg cgctctctta cggttcaagg ctgatgtggg gctctggcgcg    480 ccggcgttcg cgccgctctg cttgagaacg acgacaagg ctgcggctgc gcgcgtcggg    540
gtgccggatc tgtcgtcctt gctgtcgccg ccggcgacca tgcctcctgc ggacgccggc    600
gccgaggaga gccgtcgcca ggttgtggga tttgcgcaag ctgcggccag gcggctgcc    660 atggcgccgt ctgcccatgc gcttgggcac cagtcgcagt cgcagcagca gcagcagcag    720
gcaaggaagg ctcggcgttg ctggtcgacg gagctgcatc gcaagttcgt cgccgccttg    780
gatcagctcg gtggccccca gttgccacgc cgaagcaaa tcaggagct gatgaaggtg    840 gatgggctga caaacgacga agtgaaaagc catcttcaga ataccggct gcacaaccgc    900 agggcgcctg gatccggcgt ggtgcgccag ccgatcgtgc tcgtgggagg gctgtggatt    960
ccccaggagc aaggcagccc tcagtctgga tctccccacg gccctctcca ccacttgtcc   1020
acctcggtgg ccgccgtctc gtccgccgcc accgcagct gcgaggagga agacggccgg   1080
tccgagagct atggctggaa atga                                          1104

<210> SEQ ID NO 10
<211> LENGTH: 349
<212> TYPE: DNA
<213> ORGANISM: Zea Mays

<400> SEQUENCE: 10
cagacatgct ttgcagtagt agtagtatat agggtgtgtt tggtttgact tttgactctg     60
gcttttaccc cctaaaagct aaaagccaaa ccaaagggct ggatttagga agcagctttt    120
tctaaaagcc gactttcttg cagtgcaaaa ctgaaagcac ctctagacct gcttttagct    180
gcttttagat ggaactgtga aaatatatat ggaaaaacat ttagcgactt ttagtggttt    240
ccaccaaaca cttttagct ttttaacagc tcgcagccca cagcagcttt tctcacagct    300
cacagcccac agcagctttt ttcacagcca cagtccaacc aaacagacc                349
```

<210> SEQ ID NO 11
<211> LENGTH: 20
<212> TYPE: DNA
<213> ORGANISM: Zea Mays

<400> SEQUENCE: 11
cggtctctgt tgtgggcttt            20

<210> SEQ ID NO 12
<211> LENGTH: 20
<212> TYPE: DNA
<213> ORGANISM: Zea Mays

<400> SEQUENCE: 12
atgctggcgc cttgatagtc            20

<210> SEQ ID NO 13
<211> LENGTH: 1048
<212> TYPE: DNA
<213> ORGANISM: Zea Mays

<400> SEQUENCE: 13
aattatctgg gcctaactga aactgagctg acggagcacg agcacggaag ccatgcttgt      60
tgtatacata acataagccg gggggaggat atgctcgagg cattctcttc ttcctcctcc     120
gtcagtcact ggctcggtcc attcgttagc gtctcaccag tccttgatca gcattgttaa     180
tactactagc tcgctgctga gtgctgacaa tgcgaaacag tttcttggca ggattccaac     240
tcgagctcgc cgtcgctgtc gctgtcgctg gaccgtagga acgtgccggt cccctccctg     300
catggcgggc caaagagcca cccagatcag aggacggatc cccgtgaaat cccccctctt     360
gttctttaat tactcgcagg cggaggaaag gcggcagtgc acagcgacag agagacgaag     420
actttggaat cgtccttggg tggatggatg gacggacgaa cgaggcgggg ccgcgagctc     480
tgaatattcg ccgccgtcga tgcatcggcg gcctgcctgt cgctgtcgac ggagagggtg     540
gtactggtgt gcgcaaccgg acaacgcaat gttcaggcct gaagaatcgg aatcggaata     600
ttatattccg tctggtgtgg ttgtcacttt cttttctttg tgtgtgtttt tttgttgttt     660
gttgttgttg tgtagataaa tactatgggg aagaatggag ggggatatga ggatatcctc     720
gttgattctg cttgagaaac tagggcgtat tatatgatac atacatttgg aattctcact     780
ctcggccgac cccgccggcg acctcagccc gacgtggata tataaaaaaa aagatgatta     840
aagctttgta agataagact agtctgcact ttctagtaga tttagaccat attttgaaac     900
gtctgaaact aataattaac agataaaact agctaagaga gaacgaatca gctaatagat     960
tagctaattg ctggttacat ctctcaaata gctattagtt attagttaat ttaatctagc    1020
taaaatcaaa tacaacaact tactcttt                                        1048

<210> SEQ ID NO 14
<211> LENGTH: 1048
<212> TYPE: DNA
<213> ORGANISM: Zea Mays

<400> SEQUENCE: 14
aattatctgg gcctaactga aactgagctg acggagcacg agcacggaag ccatgcttgt      60
tgtatacata acataagccg gggggaggat atgctcgagg cattctcttc ttcctcatcc     120
gtcagtcact ggctcggtcc attcgttagc gtctcaccag tccttgatca gcattgttaa     180
tactactagc tcgctgctga gtgctgacta tgcgaaacag tttcttggca ggattccaac     240

-continued

```
aactcgagct cgccgtcgcc gtcgctgtcg ctggaccgta cgaacgtgcc ggtcccctcc    300
ctgcatggcg gaccaaagag ccacccagat caggacggat ccccgtgaaa tccccctct     360 tgttctttaa ttactcgcag gcggaggaaa ggcggcagtg cacagcgaca gagagacgaa    420
gactttggaa tcgtccttgg gtgcatggat ggacggacgg acgaacgaga ggggggggccg   480 cgagctctga atattcgccg ccgtcgatgc atcggcggcc tgcctgtcgc tctcgacgga    540
gagggtggta ctggtgtgcg caaccggaca acgcaatgtt caggccagaa gaatcggaat    600
cggaatatca tattccgtct ggtgtggtgg tcactttctt ttctttgtgt gtgtgttttt    660
ttgttgttgt tgtgtagata aatactatgg ggaagaatgg aggggatatg aggatatcct    720
cgttgattct gcttgagaaa ctagggcgta ttatatgata catttggaat tctcactctc    780
ggctgggccg accccgccgg cgacctcagc ccgacgtgga tatatataaa aagatgatta    840
aagctttgta agataagact agtctgcact ttctagtaga tttagaccat attttcaaac    900
gtctaaaact aataatgaac agataaaact agctaagaga gaacgaatca gctaatagat    960
tagctaattg ttagttacat ttctcaaata gctattagtt gttagttaat ttaatctagc   1020
taaaatcaac tacaacaact tactcttt                                      1048
```

<210> SEQ ID NO 15
<211> LENGTH: 24
<212> TYPE: DNA
<213> ORGANISM: Zea Mays

<400> SEQUENCE: 15

```
gatggatgga cggacgaacg aggc                                            24
```

<210> SEQ ID NO 16
<211> LENGTH: 30
<212> TYPE: DNA
<213> ORGANISM: Zea Mays

<400> SEQUENCE: 16

```
catggatgga cggacggacg aacgagaggg                                      30
```

<210> SEQ ID NO 17
<211> LENGTH: 10105
<212> TYPE: DNA
<213> ORGANISM: Zea Mays

<400> SEQUENCE: 17

```
cggtgtgtac aaagggcagg gacgtagtca acgcgagctg atgactcgcg cttactaggc     60
attcctcgtt gaagaccaac aattgcaatg atctatcccc atcacgatga aatttcccaa    120 gattaccccgg gcctgtcggc caaggctata tactcgttgg atacatcagt gtagcgcgcg    180
tgccgcccag aacatctaag ggcatcacag acctgttatt gcctcaaact tccgtggcct    240
aaacggccat agtccctcta agaagctaac tacgagggga tggctccgca tagctagtta    300
gcaggctgag gtctcgttcg ttaacggaat taaccagaca aatcgctcca ccaactaaga    360
acggccatgc accaccaccc atagaatcaa gaaagagctc tcagtctgtc aatccttgct    420
atgtctggac ctggtaagtt tccccgtgtt gagtcaaatt aagccgcagg ctccacgcct    480
ggtggtgccc ttccgtcaat tcctttaagt ttcagccttg cgaccatact cccccggaa     540 cccaaagact ttgatttctc ataaggtgcc agcggggtcc tattagtaac accgctgat     600 ccctggtcgg catcgtttat ggttgagact aggacggtat ctgatcgtct tcgagccccc    660
```

```
aactttcgtt cttgattaat gaaaacatcc ttggcaaatg ctttcgcagt tgttcgtctt      720
tcataaatcc aagaatttca cctctgacta tgaaatacga atgccccga ctgtccctat      780 taatcattac tccgatcccg aaggccaaca caataggacc ggaatcctat gatgttatcc      840
catgctaatg tatccagagc gatggcttgc tttgagcact ctaatttctt caaagtaacg      900
gcgccggagg cacgacccgg ccagttaagg ccaggagcgc atcgccggca aagggtcga       960 gccggtcggt tctcgccgtg aggcggaccg gccggcccgg cccaaggtcc aactacgagc     1020 ttttttaactg caacaactta aatatacgct attggagctg gaattaccgc ggctgctggc    1080
accagacttg ccctccaatg gatcctcgtt aagggattta gattgtactc attccaatta     1140
ccagacacta acgcgcccgg tattgttatt tattgtcact acctcccgt gtcaggattg      1200 ggtaatttgc gcgcctgctg ccttccttgg atgtggtagc cgtttctcag gctccctctc     1260
cggaatcgaa ccctaattct ccgtcacccg tcaccaccat ggtaggcccc tatcctacca     1320
tcgaaagttg atagggcaga aatttgaatg atgcgtcgcc ggcacgaagg ccgtgcgatc     1380
cgtcaagtta tcatgaatca tcggatcggc gggcagagcc cgcgtcagcc ttttatctaa     1440
taaatgcgcc cctccggaa gtcggggttt gttgcacgta ttagctctag aattactacg      1500
gttatccgag tagcacgtac catcaaacaa actataactg atttaatgag ccattcgcag     1560
tttcacagtt cgaattagtt catacttgca catgcatggc ttaatctttg agacaagcat     1620
atgactactg gcaggatcaa ccaggtagca cgtcctcgca gacgggccag cgccggcctc     1680
cgcgcggagg cgtcgtgccg ggctggcagt cgttcattcg ggcggaccga ttcttgggcg     1740
cgtgacgcca acgcgtctcc ggccttcagc gtgagccaca tccgagacca aaagcgccag     1800
cgaggtgtcc tcggtgccgc cggccatagg ccgacggcgg cacgaggcaa acgccgcgag     1860
cgctctcgag ccgacgagcc gcaccccggg gggtgagctc gacgaaggca acgtgtatcg     1920
agcacggctt cccgtgggac gggtagcagc acgcaagcac ttctcaacgc agcaggcata     1980
ggatgcccgc acgagcgatg ggacacaggc gccgggagtc ggccgcacgg cagcgggggt     2040
cctccaagca gtcacgggtc caagacaact catgcgcctg cgtagccgct acggtcgagc     2100
catccaaagc atccctccgc gctgggcgcg cgggtctgc ttgcgaggac ggcgaccgaa      2160
ggtccaccga gcgcgggaga acggaaaac gcatcgagca acgggccatc ccacggtgca     2220
gccactcgtc cagggcgtct ggccggcggt agccagccat agccggtcgt ggctgcgtca     2280
cggccgaacc acggccggcc aggcagccaa cagcgccagc cggagctggg cgcggtaggg     2340
tgccgaccgg ccacggctag gccgcgaggg ggtgcgggc tcggccgagg agacctggag     2400
gagacgctgg aaacgctatg gtttcagcag cgtttcgccc gggtttcggc tgcacgagtt     2460
ccctacccct actatacctg aggggcatac ccctcccag gacttcgggg agttctgcct     2520
tcagaaaacc agggcatttt cccagtaccc cacgaaaccc atctaagatg gctggacaca     2580 gcgttttgc tcagaatcag gggtttcgct agcgtgaccc gttttccctc acgggtgcac      2640
ccgaacttcc acgtctcacg cggggcgacc acggagggt cccgtgccct tccacgcgcc      2700
cgttttcgcg gccgtggccg aaaatccgtt tttggcccgt tcgccatggc gaacccctcg     2760
ttttcagcca aaacgcaagg ccgaacagcc ctgccgcccg ttgccttgcg tctcctcccg     2820
ttttccctcc gttccaccgt gcctttcaac cgagacctac gtagcaggct cggtgtcttt     2880
ccacgcgctt ggacttagcc cgttttcgcg gccgtggctg aaccgctgat tcggccagc     2940 gcgccatggc gaacacctcg ttttcggccc agacgcaagg ccgaacagcc ctgccgcccg    3000
tcgccgcgcg cctcctcccg ttttccctcc gttccacctt gaccttcact ccagacatgc    3060
```

-continued

```
gctctaggtt cggaataaat atttgatttt accatatctc gcttgggcaa tgtttcatat    3120
gttatgcatg tagtatggac atggctctca aacctacaga cctagcatct tttttttaaa    3180
aaatagcgtc agcatacata ggccctctaa cccttgtctg tgtaaatccg tgagcatcct    3240
agctaggtgc ctaggtgagg aggtaccatg gttaatctat aactactgat agcagaaatc    3300
aataactctc aacaactact ccctccctcc gttctctatc ttaatatcat aaaggtttat    3360
cctaaatcaa tattttaaaa ctttaatagt taataataaa tattcataaa tattaactaa    3420
ataaaaataa aactattaca tttattatta aaacatctac tatacaatat ataaaaataa    3480
ttatttttat agagattgtt agtcaaagtt ttaaaatttt gacttagaac aaaccttcgt    3540
gaccttaaga tagggaacag atgaagtatt atatatgctg ccatgcccca tcgaaacaaa    3600
tcaagtgata ccatcaatat agctgcaaca gctgaaaact tgaaagggaa atgtgccttt    3660
gggccatttc taagtatttt tggtgattta gtgtctaaca caagtgccta agtgttgatc    3720
tatgcaaagt ggtggacaaa gtgtaaatca agtcaaaagg tatgtttcta gacttagtac    3780
attgttttat ggactgatgt attgtgtcta agtgctggaa acaggagaaa tcaaattgga    3840
aaagagatgt ctttgttcag ccaaagtctg ggtgcaccgg actgtccggt ggtgcaccag    3900
acagtgtccg gtgcgccagg cagactcagg cgaacttgct gctctcggga agtaattaac    3960
ggcgtacggc taaaattcac cggactgtcc ggtgagccaa cggtcggcca ggccaacagt    4020
cggccgggcc aacggtcggc cgcgcgatcc gcgcaggaca cgtggccgag ccaacggcta    4080
gtaggggcac cggactgtcc ggtgtggacc agacagtgtc cgatgcgcca acggctccaa    4140
ggctgccaac ggtcggcttc gccaaataag gaaggaaatc cgcaccggac tgtgcggtgg    4200
tgcaccggac agtccggtgc gccaggcgac agaaggcaag aattgccttc ccagattgct    4260
ctcaacggct cctagctgcc ttggggctat aaaagggacc cctaggcgca tggaggaaag    4320
aaccaagcat cctttgagca ttgttgatca ctcacactcc gttcttgcgc acttgttcga    4380
cattcttagt gatttgagct ccgttctagt gtgaaacttg tgatagtctc ttgagctcaa    4440
gtctgggtct tgtgtgtgcg tatttgctgt gatctttgtg tcttgtgtga gttgctcatc    4500
cctcccttac ttcgtgcttc tttgtgaaca tcaaagtgta agggcgagag gctccaagtt    4560
gtggagattc ctcgcgaacg ggatatagaa aagaaaagca aaacaccatg gtattcaagt    4620
gggtctttgg accgcttgag agggggttgat tgcaaccctc gtccgttggg acgccacaac    4680
gtggaagtag gcaagtgttg tacttggccg aaccacagga taaaccactg tgtctatttg    4740
tgttgattct gttgtggtta ttgtgtttcg ctaagactct tctctagcca cttggcatta    4800
ctgtgctaac gctgagagca cctagagggg ggggtgaata ggtgatcctg taaaacttaa    4860
acttatagcc acagaaactt ggttaatcgt tagcacaata attgccaagt ggctagagag    4920
gagtcaaaac acaataacca caagaaatca atcacagaga tgacacggtg gttatcccgt    4980
ggttcggcca agtacaaaac ttgcctactc acgttgtgg cgtcccaacg gacgagagtt    5040
gcactcaact cctctcaagt gatccaatga tcaacttgaa taccacggtg ttcttcttta    5100
ctttgatctt ttcccgtttg cgaggaatct ccacaacttg gagtctctcg cccttacaat    5160
tgaatttcac aaagaagcac ggagtaaggg agggaagcaa cacacacaaa tccacagcaa    5220
tatgcgcaca cacacggcca agaatcgagc tcaaaagact atctcaaaat tctcactaga    5280
acggagctcg aattactgag aatgacaaat gaatgcgcaa agactgagtg tggatgatca    5340
agaatgctct aaggttgctt ggataactcc tccatgcgcc taggggtccc ttttatagcc    5400
```

```
ccaaggcagc taggagccgt tgagagcaaa tctggaagac caatcttgcc ttctgtcgtc    5460
gggtgcaccg gacaatccgg tgcacaccgg acactgtccg gtgcccgatt tctttcctta    5520
aacggcgcag tcgaccgttg ccgaccgttg cagatctggg agccgttggc gcaccggaca    5580
tgtccggtgc acaccggaca gtccggtgcc cccttccgac cgttggccag ccacgtgtc     5640 gcgcgcagat tccgcggccg accgttggct cggccgaccg ttggctcacc ggacagtccg    5700
gtgcacaccg acagtccggt gaattatagc cgtacgccat cggcgaatt cccgagagcg     5760 gccacttcgc gccgtgtcag cctggcgcac cggacactgt ccggtgcacc accggacagt    5820
ccggtgtgct agaccgagct gagtcttggc tgtacacagc caagtctttg cacctttctt    5880
cttttctttt tctttctgtt tctaacactt agacaagtat attagtacac aaaaccaatg    5940
tactaaggct tagaaacata cctttactca tgatttgcac tttgttcatc catgggcata    6000
gattcacatt taagcacttg tgttggcact caatcaccaa aatactttag aaatggccca    6060
aaggcacatt tcccttttcaa tctccccctt tttggtgatt tatgccaaca caacataaag    6120
caactagaac aagtgcaata tcacttcaaa taaaaataat tttgagtttt attcgatctt    6180
ggcatatatg gatcatcctt tgccaccact tggtttgttt ttgcaaatca aacacaaaat    6240
cctatctcta agtcaaatcc acttgtagag acacaaagag aggttttcca agaaaattg     6300 attcaagatt ccaaaaactc cccctttttc ccataatcaa cacttctccc acaagagacc    6360
aacttttgac aaaagagaca atgcaagagt tttgaccaca caaaagctct aatctactat    6420
tttcaaaatt ctcaagtggt agctgatcca tttattgctt tggcctttat tttctccccc    6480
tttggcatca agcaccaaaa cgggattaat cttggcccta gaaccccatt gcctcaccaa    6540
aatcttcaac gaagaacaaa tagcaataag agttcatgag gtgaacttgg aataagttac    6600
cctctcatcg gagtgcagtg gaagtctttc atggtccaag tccacctttt ccctttcaat    6660
tctccttcga gactaaataa cgcaaactca agcatatggt tagtctcaaa agggtcaagt    6720
tgtaacacaa ctcccccaaa atatgtgcat cacttacaca aggacttgtg aggtccaggg    6780
aatgtttgta caacttgagc accacaataa gcaacaaaaa tgcagaatga acatgatcaa    6840
aggcataaac acatgtatgc tacaattcaa tccaagttcc gcgaatctaa gacatttagc    6900
tcactacgca gcctgcaaaa ggtcttctca tctagaggct tggtaaagat atcggctagc    6960
tggttctcgg tgctaacatg aaacacttcg atatctccct tttgctggtg gtctctcaaa    7020
aagtgatgcc ggatgtctat gtgctttgtg cggctgtgct caacaggatt ctccgccatg    7080
cggatagcac tctcattatc acataggagt gggactttgc tcagattgta gccaaagtcc    7140
cggagggttt gcctcatcca agtagttgc gcgcaacact gtcctgcggc aacatactcg     7200
gcctcagcgg tggatagggc aacggaggtt tgtttcttag atttccacga caccagggac    7260
cttcctaaga attggcacgt ccctggtgta ctctttctat cgaccttaca tccagcatag    7320
tcggaatctg aatatccaat caagtcaaag gtagacccct ttggatacta gagcccgaag    7380
caaggcgtag ccaccaaata tctaagaatt cgcttcaccg ccactaagtg acactcctta    7440
ggatcggatt gaaatctagc acacatgcat acgctaagca taatatccgg tctactagca    7500
cataaataaa gtaagacccc tatcattgac cggtatgctt tttgatcaac ggacttacct    7560
cctttgttga ggtcggtgtg tccgtcggtc cccatcggag tctttgcggg cttggcgtcc    7620
ttcatcccaa accgctttag cagatcttgc gtgtacttcg tttgggagat gaaggtgccg    7680
tccttgagtt gcttcacttg gaacccaagg aagtagttca actcgcccat cattgacatc    7740
tcgaatttct gcgtcatcac cctgctaaac tcttcacaag acttttggtt agtagaacca    7800
```

```
aatattatgt catcgacata aatttggcac acaaacaaat caccatcaca tgtctttgta    7860
aaaagagttg gatcggcttt cccaaccttg aaagcattaa caattagaaa gtctctaagg    7920
cattcatacc atgctcttgg ggcttgctta agtccataga gcgccttaga gagcttacac    7980
acgtggtcgg ggtaccgttc atcctcgaag ccagggggtt gctccacgta cacctcctcc    8040
ttgattggcc cattgaggaa agcgctcttc acatccattt ggaacaacct gaaagaatgg    8100
tgagcggcat atgctagcaa gatacgaatg gactctagcc tagccacagg agcaaaagtc    8160
tcctcaaagt ccaaacctgc gacttgggca taaccttttg ccacaagtcg agccttattc    8220
cttgtcacca ctccgtgctc gtcttgtttg ttgcggaaca cccacttggt tcccacaaca    8280
ttttgcttag gacgaggcac cagcgtccaa acttcattgc gcttgaagtt gttgagttcc    8340
tcctgcatgg ccaacaccca gtccggatct agcaaggcct cttctatcct gaaaggctca    8400
atagaagaga caaggagta atgctcacaa aaattaacta atcgagatcg agtagttact    8460
cccttgctaa tgtcacccag aatttggttg acgggatgat ccctttgaat catcgctcga    8520 acttggttg gaggtgccgg ttccgcttct tcctccatca catgatcatc ttgtgctccc    8580
ccttgatcac acgcctcctg ttgatgaacc tgttcatcgt cttgagttgg gggatgcacc    8640
attgttgagg aagaaggttg atctcgttca tcttgttcct gtggccgaac ttctccaatc    8700
gccatggttc gaatagcggc cgtcggaaca tcttcttcat ctacatcatc aagatcaaca    8760
atttgctctc ttggagagcc attagtctca tcaaatacaa cgtcgctaga gacttcaacc    8820
aaacccgatg atttgttgaa gactctatac gcctttgtat ttgagtcata acctaacaaa    8880
aacccttcta cagctttggg agcaaactta gaatttctac ccttctttac tagaatgtag    8940
cacttgctcc caaatacacg aaagtaagat acattgggtt tgttaccggt tagtagctca    9000
tacgacgtct tcttgaggag gcgatgaagg tagaccctgt tgatggcgtg gcaagccgtg    9060
ttcacggctt cagtccaaaa gcactcgggg gtcttgaact ctcctagcat cgtcctcgcc    9120
atatcgatga gcgtcctgtt cttcctttct accacaccgt tttgctgtgg tgtgtaggga    9180
gcggagaact tgtgcttgat cccttcctct tcaggaact cctccacttg aaggttcttg    9240
aactcggacc cgttgtcgct ccttatcttc tttactttga gctcaaactc attttgagct    9300
ctcctgagga agcgcttgag ggtcccttgt gtttcagact tatcctgcaa aaagaacacc    9360
caagtgaagc gggaaaagtc atcaacaata actagacctt acttacttcc tcctatgctc    9420
agataggcga cgggtccgaa gaggtccata tgtagcagct ccagtggtct tgaggtggtc    9480
atcacattct tgctgtgatg tgttcctccc acttgtttac ctgcttgaca cgctgcacaa    9540
ggtctatctt tttcgaattg aacgttagtc aaacctatta cgtgttctcc ctttagaagc    9600
ttgtgaaggt tcttcatccc cacatgtgct aagcggcgat gccacagcca gcccatgcta    9660
gtcttagcta ttaagcatgc atctagaccg gcctcttctt ttgcaaaatc aactaaataa    9720
agtttgtcgt ctaatacacc cttaaaagct actgaaccat cacttcttct aaagacagac    9780
acatctacat ttgtaaatag acagttatat cccatattgc ataattgact aaccgatagc    9840
aaattatatc ctagagactc tactaaaaac acattagaga tagagtgctc attagagatt    9900
gcaattttac ctaacccttt tatcttgcct tgattcccat caccgaatat gattgaatct    9960
tgggaatcct tattcttgac gtaggaggtg aacatcttct tctccccgt catatggttt    10020 gtgcatccgc tgtcaataat ccagcttgaa cccccggatg cataaacctg caaggcaaat    10080
ttaggcttgg gttttaggta cccaa                                         10105
```

<210> SEQ ID NO 18
<211> LENGTH: 1652
<212> TYPE: DNA
<213> ORGANISM: Zea Mays

<400> SEQUENCE: 18

```
cggtgtgtac aaagggcagg gacgtagtca acgcgagctg atgactcgcg cttactaggc        60
attcctcgtt gaagaccaac aattgcaatg atctatcccc atcacgatga aatttcccaa       120
gattacccgg gcctgtcggc caaggctata tactcgttgg atacatcagt gtagcgcgcg       180
tgccgcccag aacatctaag ggcatcacag acctgttatt gcctcaaact tccgtggcct       240
aaacggccat agtccctcta agaagctaac tacgaggga tggctccgca tagctagtta       300
gcaggctgag gtctcgttcg ttaacggaat taaccagaca aatcgctcca ccaactaaga       360
acggccatgc accaccaccc atagaatcaa gaaagagctc tcagtctgtc aatccttgct       420
atgtctggac ctggtaagtt tccccgtgtt gagtcaaatt aagccgcagg ctccacgcct       480
ggtggtgccc ttccgtcaat tcctttaagt ttcagccttg cgaccatact cccccggaa       540
cccaaagact ttgatttctc ataaggtgcc agcggggtcc tattagtaac acccgctgat       600
ccctggtcgg catcgtttat ggttgagact aggacgtat ctgatcgtct tcgagccccc       660
aactttcgtt cttgattaat gaaaacatcc ttggcaaatg ctttcgcagt tgttcgtctt       720
tcataaatcc aagaatttca cctctgacta tgaaatacga atgcccccga ctgtccctat       780
taatcattac tccgatcccg aaggccaaca caataggacc ggaatcctat gatgttatcc       840
catgctaatg tatccagagc gatggcttgc tttgagcact ctaatttctt caaagtaacg       900
gcgccggagg cacgacccgg ccagttaagg ccaggagcgc atcgccggca gaagggtcga       960
gccggtcggt tctcgccgtg aggcggaccg gccggcccgg cccaaggtcc aactacgagc      1020
tttttaactg caacaactta aatatacgct attggagctg gaattaccgc ggctgctggc      1080
accagacttg ccctccaatg gatcctcgtt aagggattta gattgtactc attccaatta      1140
ccagacacta acgcgcccgg tattgttatt tattgtcact acctcccgt gtcaggattg      1200
ggtaatttgc gcgcctgctg ccttccttgg atgtggtagc cgtttctcag gctccctctc      1260
cggaatcgaa ccctaattct ccgtcacccg tcaccaccat ggtaggcccc tatcctacca      1320
tcgaaagttg atagggcaga aatttgaatg atgcgtcgcc ggcacgaagg ccgtgcgatc      1380
cgtcaagtta tcatgaatca tcggatcggc gggcagagcc cgcgtcagcc ttttatctaa      1440
taaatgcgcc cctcccggaa gtcggggttt gttgcacgta ttagctctag aattactacg      1500
gttatccgag tagcacgtac catcaaacaa actataactg atttaatgag ccattcgcag      1560
tttcacagtt cgaattagtt catacttgca catgcatggc ttaatctttg agacaagcat      1620
atgactactg gcaggatcaa ccaggtaccc aa                                    1652
```

<210> SEQ ID NO 19
<211> LENGTH: 10674
<212> TYPE: DNA
<213> ORGANISM: Zea Mays
<220> FEATURE:
<221> NAME/KEY: misc_feature
<222> LOCATION: (3089)..(3188)
<223> OTHER INFORMATION: n is a, c, g, or t

<400> SEQUENCE: 19

```
ccgacgccgc cggagatttt atctcgccgc cgttccacac acaccgcgac gtggacagcc        60
agcaccgctg ttattcttga accacggtat gagttcgttt gcttgcaatt gcaatagtcc       120
```

```
agcttctagt tgttcgatc tatgtgcgta ttggcctgtg gtagtttctt tcttaggccg    180
tcgtttgggc ggggcgcgcc aggaaggagc agtctgcatc taataatcac ttgaacccaa    240
ttcaattcag tatatacaat tcttcttata tagacggaga catccatcta ctttcatcta    300
acatcatttt acacctgttt tgcttaaatt ctagatatac ttattacact tagcttgtga    360
ttcaacaggt accgtaccgt catgggcatg ttgatgaaca acgacgacag cagcagcagc    420
aggactagca tgcatccacg gccgcaggtc cttgcttccc tgcccttgct ggtctacgaa    480
tacgaggatc atcccaatgc cacaacaagg atgctcatat atagcctacc cgagcggagc    540
attgtctaca cgcacaacag cagtaggccc cagatgatga tgatggaggg taacttatcc    600
ttcagcaccc ctcaaggatg gctggtcatc cttggacaag cgtcagaggc ctcgatctgg    660
catccgctca ccggagagac catcacgctc ccaccaatac acggcgacca ccgtatcccc    720
gatagctgca agtgtctgct cacccgcagc tccgtcgccc acccggactg cgccgtcgtg    780
cttctcgacg tcaacgatcc tctcatgtgg ttctgccggg tgaatggcgg ggccgacagg    840
atgtgggtgc agcacgccta cgacattggc gaccactact ccccgagga gttccgcact    900 ccctccacgc ccaccaagaa tgttgtcgac gacgtcgccg cgctgggagg gaagctgtat    960
tttcgcttca ccgaatcaga ccaagacttc atgggcgtct ttgacttcga tttccatggc   1020
catactcccg ccgtggagtt ttacgagttt gatgtctccg aagagttcaa cctcaagttt   1080
cccgagggcg tgtgctctgc ctccatccac ttggtggagt ccatggatga gcttttttgct   1140 gtctgcatct tctatgtcga ttttgatccc accaacatta gcgccgctca tatcttcaag   1200
atggaggaaa tctgcgacga ggaacccgtg gcctggcacc gggtggatga tattggcgac   1260
agggctttcc tcctgacggg caccaacatg tcaacttggt gctctgcaag cacgaataac   1320
ctgaaaggga actccctcta ctttctaggc cacttagtag ctggccacag gaatctctgc   1380
atctatgata ttcaggagca atccatggag attgtccagg ttcacgacca agaagatatg   1440
gagatcgtgc gcacaccgcc atactggatt aatgtacctc cgtgctagta ttagcctatt   1500
acaatgtaat ttgcttaatt aatgtagctt gcttgctagc tagtgctatt tactgctgcc   1560
actactatat agtatattga atcaataaaa atagagtttg ctcgggtttt tgcattatcc   1620
gtgtatgaag ttttagaaga ggatttagca tctcaatttt ttttggga caatgtacat     1680 catctatagg tatgtgtttg cactgaataa ggggtgattg gttctgtagc acaggtcttc   1740
ttccattgtg gcctaaaaga ctcagcaata ccagccctgt ctctataagc atgtcatatt   1800
caaggagata atatactttt tattactctc ttcctttttt cggtggtaaa aaaaccctc    1860 ccatctcttc tttaataatt agaggggct acaatttctc gtttcgttaa tgtctactgt    1920
agtgcacagt ctctgtgatt tggtacagta ctgttttctg aaatctcatg gtttgttcat   1980
atcagtggtg atgcggtacc tctgtgttat gtgctagcgc ttgtttcatt agctagcctt   2040
agcttaaggc gtccagtaaa tattatattg tctgtgaatt ttatgtgctt caggttggtg   2100
tattattggt gctagattct gaagaacttg ccacaaaatg gagattgtcc aggttcacga   2160
ccagaaagat ttggaaatcg tgcgcacaca gccatcctgg attgtcgata ccgccatgct   2220
aagtcgatta caatgtactt gcttaattaa tgtaggttgc tactagtgat tgcgctaatt   2280
cggccggctg cttctctcat ggtcgtccgc tcacttggga actgacgttt acaagacaga   2340
actacttcta ctagggataa caagcacggg tgaactgttg ttgaggccgg cttgcagtca   2400
tcctgtagcg aagcgtcaat cacttgcagt agtatctcgt ctgggaagct cctctcgacc   2460
```

```
aagctagtaa tgctgagtac gttttcaatc atagggtccg ttggtctctt cccggtcaac   2520
atctgtaaaa gtaaaactcc aaaactgtac acatccaagt gaggttgtgc tgtatgctgc   2580
gtctcgtcca gtcgtcgttg tggtacgata gaagctcgca atgccgaagt cccctagacg   2640
agcgttcatg tcatatcatc gaggaggaca ttactcggct tcacatcacc ttcaaatcta   2700
ttccccgcta gggtcagaga tgacaaccga gtaagatcca atggcggacc taggttttttt   2760 ttttttttgta tagggtatgc ctcaataaaa cttttacata caattctata taatatactc   2820
catcggttcc aaaatagtat tacttttagc tcttggcttt tatgtcaaca ttcaaatgta   2880
tagcgatgaa tctagacaca taaaatacat acaacaaaca ttttatgaac caattaatta   2940
cctaaaacga attttaattt aggatagaga gagagtacat ataattttat agtaaattca   3000
ataaccaact cggtaaatag aaataaagtc atagtacatc aactagtaac aagcaacaa   3060 ttaacaacgc catctaagtc gctgcatann nnnnnnnnnn nnnnnnnnnn nnnnnnnnnn   3120
nnnnnnnnnn nnnnnnnnnn nnnnnnnnnn nnnnnnnnnn nnnnnnnnnn nnnnnnnnnn   3180
nnnnnnnnat gtcttggtga agggcacggt ggaacggagg gaaaacgaca cggaggcacg   3240
cgacgacggg cggcaggggc gttcggcctt gcgtctgggc tggaaacgag gggttcgcca   3300
tggcgcgcgg gccgaaaacg gaggcttggg cacgaactcg aaaataagct aagtccaagc   3360
gtgtggaaag acaccgaacc taaagtgcat gtcttgagtg aagggcaagg tggaacggag   3420
ggaaaattgg aggaggcgcg cctcgacggg cggcagggcc gttcggcctt gcgtattggc   3480
tgaaaacgag gggttcgcca tggcgcgcgg gccgaaaaaa acggttcggc cacggccgcg   3540
aaaacgagct aagtcccggc gtgtggaaag acaccgaacc tagagcgcat gtctggagtg   3600
aaggtgaagg tggaacggag ggaaaacggg aggaggcgcg cggcgacggg cggcagggct   3660
gttcggcctt gcgtatgggc tgaaaacgag gtgttcgcca tggcgcgcgg gccgaaaaca   3720
acggttcggc cacggccgcg aaaacgggct aagtccaagc gcgtggaaag acaccgaggc   3780
tgctacgtag gtctcggttg aagggcacgg tggaacggag gaaaacggg aggagacgca   3840 aggcaacagg cggcagggct gttcggcctt gcgttttggg tgaaaacgag gggttcgcca   3900
tggcgaacgg gccaaaaacg gattttggc cacggccgcg aaaacgggca cgtggaaggg   3960
cacaggaccc tcccgtggtc accccgcgtg agacgtggaa gttcgggtcc acccgtgagg   4020
gaaaacgggt cacgctagcg aaaccccctga ttctgagcaa aaacgctgtg tccagccatc   4080
ttagatgggt ttcgtggggt actgggaaaa tgccctggtt ttctgaaggc agaactcccc   4140
gaagtcctgg gaggggtat gcccctcagg tatagtaggg ggtagggaac tcgtgcagcc   4200
gaaacccggg cgaaacgctg ctgaaaccat agcgtttcca gcgtctcctc caggtctcct   4260
cggccgagcc ccgcaccccc tcgcggccta gccgtggccg gtcggcaccc taccgcgccc   4320
agctccggct ggcgctgttg gctgcctggc cggccgtggt tcggccgtga cgcagccacg   4380
accggctatg gctggctacc gccggccaga cgccctggac gagtggctgc accgtgggat   4440
ggcccgttgc tcgatgcgtt ttccgtttct cccgcgctcg gtggaccttc ggtcgccgtc   4500
ctcgcaagca gacccgccgc gcccagcgcg gagggatgct ttggatggcc cgaccgtagc   4560
ggctacgctg gcgcatgagt tgtcttggac ccgtgactgc ttgaggacc cccgctgccg   4620 tgcggccgac tcccggcgcc cgtgtcccat cgctcgtgcg ggcatcctgt gcctgctgcg   4680
ttgagaagtg cttgcgtgct gctaccccgtc ccacgggaag ccgtgctcga tacacgttgc   4740
cttcgtcgag ctcacccccc ggggtgcggc tcgtcggctc gagagcgccc gcggcgtttg   4800
cctcgtgccg ccgtcggcct atggccggcg gcaccgagga cacctcgctg gcgcttttgg   4860
```

-continued

```
tctcggatgt ggctcacgct gaaggccgga gacgcgttgg cgtcacgcgc ccaagaatcg    4920
gtccgcccga atgaacgacg gccagcccgg cacgacgcct ccgcgcggag gccggcgctg    4980
gcccgtctgc gaggacgtgc tacctggttg atcctgccag tagtcatatg cttgtctcaa    5040
agattaagcc atgcatgtgc aagtatgaac taattcgaac tgtgaaactg cgaatggctc    5100
attaaatcag ttatagtttg tttgatggta cgtgctactc ggataaccgt agtaattcta    5160
gagctaatac gtgcaacaaa ccccgacttc cggggggggc gcatttatta gataaaaggc    5220
tgacgcgggc tctgcccgcc gatccgatga ttcatgataa cttgacggat cgcacggcct    5280
tcgtgccggc gacgcatcat tcaaatttct gccctatcaa ctttcgatgg taggataggg    5340
gcctaccatg gtggtgacgg gtgacggaga attagggttc gattccggag agggagcctg    5400
agaaacggct accacatcca aggaaggcag caggcgcgca aattacccaa tcctgacacg    5460
gggaggtagt gacaataaat aacaataccg ggcgcgttag tgtctggtaa ttggaatgag    5520
tacaatctaa atcccttaac gaggatccat tggagggcaa gtctggtgcc agcagccgcg    5580
gtaattccag ctccaatagc gtatatttaa gttgttgcag ttaaaaagct cgtagttgga    5640
ccttgggccg ggccggccgg tccgcctcac ggcgagaacc gaccggctcg acccttctgc    5700
cggcgatgcg ctcctggcct taactggccg ggtcgtgcct ccggcgccgt tactttgaag    5760
aaattagagt gctcaaagca agccatcgct ctggatacat tagcatggga taacatcata    5820
ggattccggt cctattgtgt tggccttcgg gatcggagta atgattaata gggacagtcg    5880
ggggcattcg tatttcatag tcagaggtga aattcttgga tttatgaaag acgaacaact    5940
gcgaaagcat ttgccaagga tgttttcatt aatcaagaac gaaagttggg ggctcgaaga    6000
cgatcagata ccgtcctagt ctcaaccata acgatgccg accagggatc agcgggtgtt    6060
actaatagga ccccgctggc accttatgag aaatcaaagt ctttgggttc cggggggagt    6120
atggtcgcaa ggctgaaact taaaggaatt gacggaaggg caccaccagg cgtggagcct    6180
gcggcttaat ttgactcaac acggggaaac ttaccaggtc cagacatagc aaggattgac    6240
agactgagag ctcttttcttg attctatggg tggtggtgca tggccgttct tagttggtgg    6300
agcgatttgt ctggttaatt ccgttaacga acgagacctc agcctgctaa ctagctatgc    6360
ggagccatcc ctccatagtt agcttcttag agggactatg gccgtttagg ccacggaagt    6420
ttgaggcaat aacaggtctg tgatgccctt agatgttctg ggccgcacgc gcgctacact    6480
gatgtatcca cgagtatat agccttggcc gacaggcccg ggtaatcttg gaaatttca    6540
tcgtgatggg gatagatcat tgcaattgtt ggtcttcaac gaggaatgcc tagtaagcgc    6600
gagtcatcag ctccgttgac tacgtccctg ccctttgtac acaccgcccg tcgctcctac    6660
cgattgaatg gtccggtgaa gtgttcggat cacggcgacg ggggcggttc gccgcccccg    6720
acgtcgcgag aagtccattg aaccttatca tttagaggaa ggagaagtcg taacaaggtt    6780
tccgtaggtg aacctgcgga aggatcattg ccgtgaccct aaacaaaac agaccgcgaa    6840
cgagtcaccc gtgccgccgg gctccggccc ggcacgctgc ccccccgaa cctcccgcgg    6900
ggaagggggg tgccgcgaaa aagaacccac ggcgccccgg gcgccaagga acaccagtac    6960
tacctcctgc cccgcggagc ggtcggcccg ccttccgctc ccagggcagc ggttacacct    7020
taatcgacac gactctcggc aacggatatc tcggctctcg catcgatgaa gaacgtagca    7080
aaatgcgata cctggtgtga attgcagaat cccgcgaacc atcgagtttt tgaacgcaag    7140
ttgcgcccga agccttctgg cggagggcac gtctgcctgg gcgtcacgcc aaaagacact    7200
```

```
cccaacaccc ccccgcgggg cgagggacgt ggcgtctggc cccccgcgcc gcagggcgag      7260
gtgggccgaa gcaggggctg ccggcgaacc gcgccgggcg cagcacgtgg tgggcgacat      7320
caagttgttc tcggtgcagc gtcacggcgc gcggccggac attcggccct aaggacccat      7380
cgagcgaccg agcttgccct cggaccgcga ccccaggtca gtcgggacta cccgctgagt      7440
ttaagcatat aaataagcgg aggagaagaa acttacgagg attcccctag taacggcgag      7500
cgaaccggga gcagcccagc ttgagaatcg ggcggcctcg ccgcccgaat tgtagtctgg      7560
agaggcgtcc tcagcgacgg accgggccca agttctctgg aaagggacgc ctgggagggt      7620
gagagccccg tccggcccgg accctgtcgc accacgaggc gccgtcaacg agtcgggttg      7680
tttgggaatg cagcccaaat cgggcggtaa actccgtcca aggctaaata caggcgagag      7740
accgatagcg aacaagtacc gcgagggaaa gatgaaaagg actttgaaaa gagagtcaaa      7800
gagtgcttga aattgccggg agggaagcgg atggggctg gcgacgcgca ccggccgtat      7860
gcggaacggc tcctgctggt ccgccgatcg gctcggggcg tggaccgttg tcgcccgcgc      7920
cggcggccaa agcccggggg ccctaggcgc ccccggcagc cgtcgtcggc gcggacggta      7980
tccgcgcgcc tctggcgcgc ccctcggggc gctgcgccgc aacggcctgc gagctcccca      8040
tccgacccgt cttgaaacac ggaccaagga gtctgacatg cgtgcgagtc gacgggttca      8100
gaaacctgag atgcgcaagg aagctgacga gcgggaggcc ctcacgggcc gcaccgctgg      8160
ccgaccctga tcttctgtga agggttcgag ttggagcacg cctgtcggga cccgaaagat      8220
ggtgaactat gcctgagcgg ggcgaagcca gaggaaactc tggtggaggc tcgaagcgat      8280
actgacgtgc aaatcgttcg tctgacttgg gtataggggc gaaagactaa tcgaaccatc      8340
tagtagctgg ttccctccga agtttccctc aggatagctg gagcccacac gagttctatc      8400
gggtaaagcc aatgattaga ggcatcgggg gcgcaacgcc ctcgacctat tctcaaactt      8460
taaataggta ggacggcgcg gctgcttcgg tgagccgtgc cacggaatcg ggagctccaa      8520
gtgggccatt tttggtaagc agaactggcg atgcgggatg aaccggaagc cgggttacgg      8580
tgccaaactg cgcgctaacc tagaacccac aaagggtgtt ggtcgattaa gacagcagga      8640
cggtggtcat ggaagtcgaa atccgctaag gagtgtgtaa caactcacct gccgaatcaa      8700
ctagccccga aaatggatgg cgctgaagcg cgcgacccac accggccat ctgggcgagc      8760 gacatgcccc gatgagtagg agggcgcggc ggccgccgca aaaccggggg cgcgagcccg      8820
ggcggagcgg ccgtcggtgc agatcttggt ggtagtagca aatattcaaa tgagaacttt      8880
gaaggccgaa gaggagaaag gttccatgtg aacggcactt gcacatgggt aagccgatcc      8940
taagggacgg gggaaacccg gcagatagcg cgatcacgcg cgtcacccga aagggaatcg      9000
ggttaagatt tcccgagccg ggacgtggcg gcagacggcg acgttaggaa gtccggagac      9060
gccggcgggg gcctcgggaa gagttatctt ttctgcttaa cggcccgcca accctggaat      9120
cggttcagcc ggaggtaggg tccagcggcc ggaagagcac cgcacatcgc gcggtgtccg      9180
gtgcgccccc ggcggccctt gaaaatccgg aggaccgaat accgtccacg cccggtcgta      9240
ctcataaccg catcaggtct ccaaggtgaa cagcctctgg ccaatggaac aatgtaggca      9300
agggaagtcg gcaaaacgga tccgtaactt cgggaaaagg attggctctg agggttgggc      9360
tcgggggtcc cggccccgaa cccgtcggct gctggcggaa tgctcgagct gctcgcgcgg      9420
cgagagcggg ccgccgcgtg ccggccgggg gacggaccgg gaacggcccc tcgggggcc      9480 ttccccgggc gtcgaacaac cgactcagaa ctggtacgga caaggggaat ccgactgttt      9540
aattaaaaca aagcattgcg atggtcctcg aggatgctga cgcaatgtga tttctgccca      9600
```

```
gtgctctgaa tgtcaaagtg aagaaattca accaagcgcg ggtaaacggc gggagtaact      9660
atgactctct taaggtagcc aaatgcctcg tcatctaatt agtgacgcgc atgaatggat      9720
taacgagatt cccactgtcc ctgtctacta tccagcgaaa ccacagccaa gggaacgggc      9780
ttggcggaat cagcgggaa agaagaccct gttgagcttg actctagtcc gactttgtga       9840
aatgacttga gaggtgtagg ataagtggga gcctccgggc gcaagtgaaa taccactact      9900
tttaacgtta ttttacttat tccgtgggtc ggaagcgggg caccgcccct ccttttggct      9960
ccaaggcccg gcctcgccgg gccgatccgg gcggaagaca ttgtcaggtg gggagtttgg     10020
ctggggcggc acatctgtta aaagataacg caggtgtcct aagatgagct caacgagaac     10080
agaaatctcg tgtggaacaa aagggtaaaa gctcgtttga ttctgatttc cagtacgaat     10140
acgaaccgtg aaagcgtggc ctatcgatcc tttagacctt cggagtttga agctagaggt     10200
gtcagaaaag ttaccacagg gataactggc ttgtggcagc caagcgttca tagcgacgtt     10260 gcttttgat cctcgatgt cggctcttcc tatcattgtg aagcagaatt caccaagtgt       10320
tggattgttc acccaccaat agggaacgtg agctgggttt agaccgtcgt gagacaggtt     10380
agttttaccc tactgatgac cgcgccgcga tagtaattca acctagtacg agaggaaccg     10440
ttgattcaca caattggtca tcgcgcttgg ttgaaaagcc agtggcgcga agctaccgtg     10500
tgccggatta tgactgaacg cctctaagtc agaatccaag ctagcaaccg gcgcctctgc     10560
tcgccgcccg ccccgaccca cgttagggcg ttcgcgcccc aagggcccgt gccattggct     10620
cagcccgccc ggccgacgcg ccgcggcggg ccgcctcgaa gctcccttcc caac           10674

<210> SEQ ID NO 20
<211> LENGTH: 674
<212> TYPE: DNA
<213> ORGANISM: Zea Mays

<400> SEQUENCE: 20
tacctggttg atcctgccag tagtcatatg cttgtctcaa agattaagcc atgcatgtgc        60
aagtatgaac taattcgaac tgtgaaactg cgaatggctc attaaatcag ttatagtttg       120
tttgatggta cgtgctactc ggataaccgt agtaattcta gagctaatac gtgcaacaaa       180
ccccgacttc cggagggggc gcatttatta gataaaaggc tgacgcgggc tctgcccgcc       240
gatccgatga ttcatgataa cttgacggat cgcacggcct tcgtgccggc gacgcatcat       300
tcaaatttct gccctatcaa ctttcgatgg taggataggg gcctaccatg gtggtgacgg       360
gtgacggaga attagggttc gattccggag agggagcctg agaaacggct accacatcca       420
aggaaggcag caggcgcgca aattacccaa tcctgacacg gggaggtagt gacaataaat       480
aacaataccg ggcgcgttag tgtctggtaa ttggaatgag tacaatctaa atcccttaac       540
gaggatccat tggagggcaa gtctggtgcc agcagccgcg gtaattccag ctccaatagc       600
gtatatttaa gttgttgcag ttaaaaagct cgtagttgga ccttgggccg ggccggccgg       660
tccgcctcac ggcg                                                         674

<210> SEQ ID NO 21
<211> LENGTH: 721
<212> TYPE: DNA
<213> ORGANISM: Zea Mays
```

<400> SEQUENCE: 21

```
tacctggttg atcctgccag tagtcatatg cttgtctcaa agattaagcc atgcatgtgc      60
aagtatgaac taattcgaac tgtgaaactg cgaatggctc attaaatcag ttatagtttg     120
tttgatggta cgtgctactc ggataaccgt agtaattcta gagctaatac gtgcaacaaa     180
ccccgacttc cgggaggggc gcatttatta gataaaaggc tgacgcgggc tctgcccgcc     240
gatccgatga ttcatgataa cttgacggat cgcacggcct tcgtgccggc gacgcatcat     300
tcaaatttct gccctatcaa ctttcgatgg taggataggg gcctaccatg gtggtgacgg     360
gtgacggaga attagggttc gattccggag agggagcctg agaaacggct accacatcca     420
aggaaggcag caggcgcgca aattacccaa tcctgacacg gggaggtagt gacaataaat     480
aacaataccg ggcgcgttag tgtctggtaa ttggaatgag tacaatctaa atcccttaac     540
gaggatccat tggagggcaa gtctggtgcc agcagccgcg gtaattccag ctccaatagc     600
gtatatttaa gttgttgcag ttaaaaagct cgtagctcga cccttctgcc ggcgatgcgc     660
tcctggcctt aactggccgg gtcgtgcctc cggcgccgtt actttgaaga aattagagtg     720
c                                                                     721
```

<210> SEQ ID NO 22
<211> LENGTH: 10611
<212> TYPE: DNA
<213> ORGANISM: Zea Mays

<400> SEQUENCE: 22

```
accacataaa aacattcccc ctagagtagc tgttaatacg aataacagaa actctgttat      60
agccatttct gtacattcaa tgtactctac ggatagagga atacataaag ttgaacataa     120
taaaataaga aattgaaaga tttcgttgaa attgttcgtt tggaaatttc ccgaaaagct     180
aattataggt tcttctctcc atcggaacaa tagggccgtt atgcttatta ctaaacttgt     240
tgaagagatg aaatagaacc aaggtctatc tttttgatca gaggttaaat cgatcatcag     300
aagaagaatt aggccaaaaa ttaggataca ttctgggaaa atgaaacttc catggaagag     360
aagcaaatga aacgctttca taaaaattct cgtagaatcg agaatgaagt tttcattctg     420
tacatgccag atcatgaatt agtaactgca gccaatctcc gaaaagtccc gattgtttcg     480
atttttggaa tgggatattt acggaatccc catgaatagg atcaaacctt attccatgct     540
atttccataa gattcctctt tcttattctt aagcaagccc ccgagagggc ttagttgatc     600
atgatttctg ttttctcttt tttttccttt ttatttgttt cgaaaaagat atcgtccgat     660
tctccttcta ttgattcttt tccgatcgag atgtatggat ccatgtgtct acatacctag     720
attctgttca tggattaacg aaaatgtgca agagctctat ttgcctctgc cattctatga     780
gtcgcttcct ttttgcgtat ggcaccccca ctccctttgg cagcatctac taattcggaa     840
cttaatttga aagccatatt tcgacccgga cgcttttggg atgcttctaa taccaacga     900
atggcaagtg ctcttccttg tttagatcct atttcaatcg gaactttccg cgtcgatcct     960
ttttttattac gtcttgtttt tactcctata ttgggagtta ctctacgtat tgcttgacgt    1020
aaaaccaata gtggatttgt ttctgtcttt tgttgaatct ttttcacggc tcgatagaga    1080
atttgataag ccaatgattt ttttccgtct ttcataatac ggttaaccac catgttaact    1140
aatcgattac gaaaaattgg atcggatttt gcggttcttt tttctgcagt acctcgacgt    1200
gacatgagcg tgaaagaggt tcaagaatcc gttttctttt tataagggct aaaaacgaat    1260
```

```
cacttatttt tttggctttt tggccccata ttgtagggtg gatctcgaaa gataggaaag   1320
atctccctcc aagccgtaca tacgactttc atcgaatacg gctttccaca gaattctata   1380
gggatctatg agatcgagta tggaattctg tttactcact ttaaattgag tatccgtttc   1440
cctccttttc ccgctaggac cggaaatcct gtattttcca tatccatacg atcgagtcct   1500
taggtttccg aaatagtgta atggaaaaag aagtgcttcg aatcattgct atttgactcg   1560
gacctgttct gaaaaagtcg aggtatttcg aattgtttgt tgacacggac aaagtaaggg   1620
aaaacctctg aaagaatttc catattgacc ttggacatat aagagttccg aatcgaatct   1680
ctttagaaag aagatctttt gtctcatggt agcctgctcc agtcccctta cgaaactttc   1740
gttattgggt tagccataca cttcacatgt ttctagcgat tcacatggca tcatcaaatg   1800
atacaagtct tggataagaa tctacaacgc actagaacgc ccttgttgac gattcttttac  1860 tgcgacagca tctagggttc ctcgaataat gcgatatctc acaccgggta aatccttaac   1920
ccttcctcct cttactaata ctacagaatg ttcttgtaaa ttatggccaa taccaggtat   1980
ataagcagtg atttcaaatc cagaggttaa tcgtactctg gcaactttac gtaaggcaga   2040
gttgggtttt tgggggttga tagtggaaaa gtcgacagat aagtcatcct tactgtccct   2100
ctacagaacc gtacatgaga ttttcacctc atacggctcc tcgttcaatt ctttcgaagg   2160
gatccttttc ctcgttcgag agtctccgcc cttcttccac tccgtcccga agactaacta   2220
agaccaattg agtcacgttt tcatgttcta attgaacact ttccatttat gattaaagga   2280
gaagattgtt cttttaccaa acatatgcgg atcaaatcac gtcttataat aagaagaaat   2340
ctttctcggt atcaatcccc ttgcccctca ttcctttgaga atcagaagga tccttttcga  2400
gtttccattt cttcattttg aatctgggct cttctatctt cgacttattt ttttggcttt   2460
attcttattt tatttcattt cgattttttcc ctcttcctct atccctatcc tctaggtaca   2520
gcgtttgcat caatagagaa cttttttcctc tgtatgaatc gatattattc caatttcttc   2580
ccgaaacttc ccaagaaaaa tcccgaattg gatccaaaat tgacgggtta atgtgagctt   2640
atccatgcgg ttaggcactc ttcaaatagg aatccatttt ctaactggct ttcgtgcttt   2700
ggtgagtcgt ccgagatcct ttcgatgacc tatgttgtgt tgaagggata tctatatgat   2760
ccgatcgatt gcataagacc cgcggtagca atagaacggg gaaagtatac agaaaagaca   2820
gttcttttcg atttcgatta tctatatatt agttcgtttc tatttctaga tatctatttc   2880
tatatatcta tatattagta ttaatatcta tatattagta ttagttatct atatatttagt  2940 attagttagt agtactattc tattagttag cgatcccggc tctgtgagtt ctttcttccg   3000
tgatgaactg tcggcaccag tcctacattt tttctctgtg gaccgaggag aaagggggct   3060
cagcaggaag aggattgtac catgagagaa gcacagaggt caacccgctt caaatatgga   3120
acatggattc tggcaatgca acggagttgg gtcctcatat cgatccgaat gaatcagtct   3180
ttctacagag gtcaatcttt gcctattagg caagaggata gcaagttcga aattctgtct   3240
cggtaggaca tggatttcta ttactatgaa attcataaat tagttaatgg ggggctacc    3300 attatccttt ttcttgtatg tgttcctaag agaaggaatt tgtccatttc atgtttcgag   3360
gtctcaaaaa aagggcgtgg aaacagatag aaactcttga atggaaattg aaaagaaatg   3420
tagccccagt tccttcggaa atggtaagat ctttggcgca agaagaaggg gcgatccata   3480
tcatcttgac ttggttctgc ttccccctctt ttttaagaa taccgagtcg ggttcttctc    3540
ctaccagtat cgaatagaac atgctgaaca agatcttctt catggaaacc cactcgattt   3600
agatcgggaa aatcgtacag attttatgaa accatgtgct atggctcgaa tccatagtca   3660
```

```
atcctatttt cgataggacc ggttgacaat tgaatccaat ttttcccatt atttgactgt    3720
ccataatagt gcggaaagaa agcccggagg aagagtggcc ttgcgtttct cgccccttty    3780
ccttaggatt cgttaattct ctttctcgat gggacgggga agggatataa ctcagcggta    3840
gagtgtcacc ttgacgtggt ggaagtcatc agttcgagcc tgattatccc taaacctaat    3900
gtgagttttt tctatttttga cttactcccc caccacgatc gaacgggaat ggataagagg    3960
cttgtgggat tgacgtgata gggtagggtt ggctatactg ctggtggcga actccaggct    4020
aataatctga agcgcatgga tacaagttat ccttggaagg aaagacaatt ccgaatccgc    4080
tttgtctacg aataaggaag ctataagtaa tgcaactatg aatctcatgg agagttcgat    4140
cctggctcag gatgaacgct ggcggcatgc ttaacacatg caagtcgaac gggaagtggt    4200
gtttccagtg gcgaacgggt gagtaacgcg taagaacctg cccttgggag gggaacaaca    4260
actggaaacg gttgctaata ccccgtaggc tgaggagcaa aaggagaaat ccgcccaagg    4320
aggggctcgc gtctgattag ctagttggtg aggcaatagc ttaccaaggc gatgatcagt    4380
agctggtccg agaggatgat cagccacact gggactgaga cacggcccag actcctacgg    4440
gaggcagcag tggggaattt tccgcaatgg gcgaaagcct gacggagcaa tgccgcgtgg    4500
aggtggaagg cctacgggtc gtcaacttct tttctcggag aagaaacaat gacggtatct    4560
gaggaataag catcggctaa ctctgtgcca gcagccgcgg taagacagag gatgcaagcg    4620
ttatccggaa tgattgggcg taaagcgtct gtaggtggct tttcaagtcc gccgtcaaat    4680
cccagggctc aaccctggac aggcggtgga aactaccaag ctggagtacg gtaggggcag    4740
agggaatttc cggtggagcg gtgaaatgca ttgagatcgg aaagaacacc aacggcgaaa    4800
gcactctgct gggccgacac tgacactgag agacgaaagc taggggagca aatgggatta    4860 gagacccag tagtcctagc cgtaaacgat ggatactagg tgctgtgcga ctcgacccgt     4920
gcagtgctgt agctaacgcg ttaagtatcc cgcctgggga gtacgttcgc aagaatgaaa    4980
ctcaaaggaa ttgacggggg cccgcacaag cggtggagca tgtggtttaa ttcgatgcaa    5040
agcgaagaac cttaccaggg cttgacatgc cgcgaatcct cttgaaagag aggggtgccc    5100
tcgggaacgc ggacacaggt ggtgcatggc tgtcgtcagc tcgtgccgta aggtgttggg    5160
ttaagtctcg caacgagcgc aaccctcgtg tttagttgcc actatgagtt tggaaccctg    5220
aacagaccgc cggtgttaag ccggaggaag gagaggatga ggccaagtca tcatgcccct    5280
tatgccctgg gcgacacacg tgctacaatg gcgggacaa agggtcgcga tctcgcgagg    5340
gtgagctaac tccaaaaacc cgtcctcagt tcggattgca ggctgcaact cgcctgcatg    5400
aagcaggaat cgctagtaat cgccggtcag ccatacggcg gtgaatccgt tcccgggcct    5460
tgtacacacc gcccgtcaca ctataggagc tggccaggtt tgaagtcatt acccttaacc    5520
gtaaggaggg ggatgcctaa ggctaggctt gcgactggag tgaagtcgta acaaggtagc    5580
cgtactggaa ggtgcggctg gatcacctcc ttttcaggga gagctaatgc ttatgcttat    5640
tgggtatttt ggtttgacac tgcttcacgc ccaaaaagaa ggcagctacg tctgagctaa    5700
acttggatat ggaagtcttc tttcgtttag ggtgaagtaa gaccaagctc atgagcttat    5760
tatcctaggt cggaacaaat tagttgatag tgataggatc cccttttttga cgtccccatg    5820 tccccccgtg tggcggcatg gggatgtcaa aaggaaaggg atggagtttt tctcgctttt    5880
ggcgtagcag gcctcccttt ggaggcccg cgcgacgggc tattagctca gtggtagagc    5940
gcgcccctga taattgcgtc gttgtgcctg ggctgtgagg gctctcagcc acatggatag    6000
```

```
ttcaatgtgc tcatcagcgc ctgacccgaa gatgtggatc atccaaggca cattagcatg    6060
gcgtactcct cctgtttgaa tcggagtttg aaaccaaaca aacttctcct caggaggata    6120 gatgggcga ttcaggtgag atcccatgta gatcgaactt tctattcact cgtgggatcc    6180
gggcggtccg ggggggggcc accgcggctc ctctcttctc gagaatccat acatcccta    6240 tcagtgtatg gagagctatc tctcgagcac aggttgaggt tcgtcctcaa tgggaaaatg    6300
gagcacctaa caacgcatct tcacagacca agaactacga gatcacccct ttcattctgg    6360
ggtgacggag ggatcgtacc attcgagcct tttttcatg cttttcccgg cggtctggag     6420
aaagcagtaa tcaataggac ttccctaatc ctcccttcct gaaggaaga acgtgaaatt     6480 cttttccctt tctgcaggga ccaggagatt ggatctagcc ataagaggaa tgcttggtat    6540
aaataagcca cttcttggtc ttcgacccc taagtcacta cgagcgcccc cgatcagtgc     6600
aatgggatgt ggctatttat ctatctcttg actcgaaatg ggagcagagc aggtttgaaa    6660
aaggatctta gagtgtctag ggttgggcca ggagggtctc ttaacccctt ctttttctg     6720 cccatcggag ttatttccca aggacttgcc gtggtaaggg ggagaagggg gaagaagcac    6780
acttgaagag cgcagtacaa cggggagttg tatgctgcgt tcgggaagga tgaatcgctc    6840
ccgaaaagga gtctattgat tctctcccaa ttggttggat cgtaggggcg atgatttact    6900
tcacgggcga ggtctctggt tcaagtccag gatggcccag ctgcgccagg gaaaagaata    6960
gaagaagcat ctgactcttt catgcatact ccacttggct cggggggat atagctcagt     7020 tggtagagct ccgctcttgc aattgggtcg ttgcgattac gggttggctg tctaattgtc    7080
caggcggtaa tgatagtatc ttgtacctga accggtggc cactttttct aagtaatggg     7140
gaagaggact gaaacatgcc actgaaagac tctactgaga caaaaagatg ggctgtcaaa    7200
aaggtagagg aggtaggatg ggcagttggt cagatctagt atggatcgta catgggcgat    7260
agttggagtc ggcggctctc ctaggcttcc ctcatctggg atccctgggg aagaggatca    7320 agttggcct tgcgaatagc ttgatgcact atctcccttc aacccttga gcgaaatgtg      7380 gcaaaaggaa ggaaaatcca tggaccgacc ccattgtctc caccccgtag gaactacgag    7440
atcaccccaa ggacgccttc ggcgtccagg ggtcacggac cgaccataga tcctgttcaa    7500
taagtggaac acattagccg tccgctctcc ggttgggcag taagggtcgg agaagggcaa    7560
tcactcgttc ttaaaaccag cattcttaag ttaagatcaa agagtcggc ggaaaaaggg     7620 gagagctccc cgttcctggt tctcctgtag ctggattccc cggaaccaca agaatccta    7680 gaatgggatt ccaactcagc accttttgtt ttgggatttt gagaagagtt gctctttgga    7740
gagcacagta cgatgaaagt tgtaagctgt gttcgggggg gagttattgc ctatcgttgt    7800
cctctatggt agaacccgtc ggggaggcct gagaggcggt ggtttaccct gtggcggatg    7860
tcagcggttc gagtccgctt atctccagcc cgtgaactta gcggatacta tgatagcacc    7920
gaaggttgcc aattcgtcag ttcgatctat gatttcgcat tcatgacgt tgataagatc      7980 cttccattta gtagcacctt aggatggcat agccttaacg ttaatggcga ggttcaaaag    8040
aggaaaggct tgcggtggat acctaggcac ccagagacga ggaagggcgt agcaagcgac    8100
gaaatgcttc gggagttga aaataagcat agatccggag attcccaaat aggtcaacct    8160
tttgaactgc ctgctgaatc catgagcagg caagagacaa cctggcgaac tgaaacatct    8220
tagtagccag aggaaaagaa agcaaaagcg attcccgtag tagcggcgag cgaaatggga    8280
gcagcctaaa ccgtgaaaac gggggttgtgg gagagcaata caagcgttgt gctgctaggc    8340
gaagcggttg agtgccgcac cctagatggc taaagtccag tagccgaaag catcactagc    8400
```

```
ttacgctctg acccgagtag catggggcac gtggaatccc gtgtgaatca gcaaggacca    8460
ccttgcaagg ctaaatactc ctgggtgacc gatagcgaag tagtaccgtg agggaaaggt    8520
gaaaagaacc cccagtgggt agtgaaatag aacgtgaaac cgtgctgagc tcccaagcag    8580
tgggagggga aagtgatctc tgaccgcgtg cctgttgaag aatgagccgg cgactcatag    8640
gcagtggctt ggttaaggga atggaaccca ccggagccgt agcgaaagcg agtcttcata    8700
gggcgattgt cactgcttat ggacccgaac ctgggtgatc tatccatgac caggatgaag    8760
cttggatgaa actaagcaga ggtccgaacc gactgatgtt gaagaatcag cggatgagtt    8820
gtggttaggg gtgaaatgcc actcgaaccc agagctagct ggttctcccc gaaatgcgtt    8880
gaggcgcagc agttgactgg acatctaggg gtaaagcact gtttcggtgc gggctgcgcg    8940
agcggtacca aatcgaggca aactctgaat actagatatg acccaaaaat aacaggggtc    9000
aaggtcggcc agtgagacga tgggggataa gcttcatcgt cgagagggaa acagcccgga    9060
tcaccagcta aggcccctaa atgaccgctc agtgataaag gaggtggggg tgcaaagaca    9120
gccaggaggt ttgcctagaa gcagccaccc tttaaagagt gcgtaatagc tcactgatcg    9180
agcgcccttg cgctgaagat gaacgggggct aagcgatctg ccgaagctgt gggatgtcaa    9240
aatgcatcgg taggggagcg ttccgcctta gagggaagca aacgcgaaag cggggggtcga    9300 cgaagcggaa gcgagaatgt cggcttgagt aacgaaaaca ttggtgagaa tccaatgccc    9360
cgaaaaccca aggtttcctc cgcaaggttc gtccacggag ggtgagtcag ggcctaagat    9420
caggccgaaa ggcgtagtcg atggacaaca ggtcaatatt cctgtactac cccttgttgg    9480
tacgagggga cggaggaggc taggttagcc gaaagatggt tataggttta aggacacaag    9540
gtgaccctgc ttttcaggg taagaagggg tagagaaaat gcctcgagcc gaggtccgag    9600
taccaagcgc tgcagcgctg aagtatgagc cccgtggact agccattgct tctccacgag    9660
gctcatacca ggcgctacgg cgctgaagta tgtaacccat gccatactcc caggaaaagc    9720
tcgaacgacc ttcaacaaaa gggtacctgt acccgaaacc gacacaggtg ggtaggtaga    9780
gaatacctag gggcgcgaga caactctctc taaggaactc ggcaaaatag ccccgtaact    9840
tcgggagaag gggtgcccccc tcgcaaaagg gggtcgcagt gaccaggccc gggcgactgt    9900
ttaccaaaaa cacaggtctc cgcaaagtcg taagaccatg tatggggggct gacgcctgcc    9960 cagtgccgga aggtcaagga agttggtgaa ctgatgacag ggaagccggc gaccgaagcc   10020
ccggtgaacg gcggccgtaa ctataacggt cctaaggtag cgaaattcct tgtcgggtaa   10080
gttccgaccc gcacgaaagg cgtaacgatc tgggcactgt ctcggagaga ggctcggtga   10140
aatagacatg tctgtgaaga tgcggactac ctgcacctgg acagaaagac cctatgaagc   10200
tttactgttc cctgggattg gctttgggct ttcctgcgc agcttaggtg gaaggcgaag   10260
aaggccccct tccgggggggg cccgagccat cagtgagata ccactctgga agagctcgga   10320
ttctaacctt gtgtcagacc cgcgggccaa gggacagtct caggtagaca gtttctatgg   10380
ggcgtaggcc tcccaaaagg taacggaggc gtgcaaaggt ttcctcgggc cagacggaca   10440
ttggtcctcg agtgcaaagg cagaagggag cttgactgca agactcaccc gtcgagcaga   10500
gacgaaagtc ggccttagtg atccgacggt gccgagtgga agggccgtcg ctcaacggat   10560
aaaagttact ctagggataa caggctgatc ttccccaaga gtccacatcg a            10611
```

<210> SEQ ID NO 23
<211> LENGTH: 611
<212> TYPE: DNA

<213> ORGANISM: Zea Mays

<400> SEQUENCE: 23

```
cccgcacaag cggtggagca tgtggtttaa ttcgatgcaa agcgaagaac cttaccaggg      60
cttgacatgc cgcgaatcct cttgaaagag aggggtgccc tcgggaacgc ggacacaggt     120
ggtgcatggc tgtcgtcagc tcgtgccgta aggtgttggg ttaagtctcg caacgagcgc     180
aaccctcgtg tttagttgcc actatgagtt tggaaccctg aacagaccgc cggtgttaag     240
ccggaggaag gagaggatga ggccaagtca tcatgcccct tatgccctgg gcgacacacg     300
tgctacaatg gcgggacaa agggtcgcga tctcgcgagg gtgagctaac tccaaaaacc      360
cgtcctcagt tcggattgca ggctgcaact cgcctgcatg aagcaggaat cgctagtaat     420
cgccggtcag ccatacggcg gtgaatccgt tcccgggcct tgtacacacc gcccgtcaca     480
ctataggagc tggccaggtt tgaagtcatt acccttaacc gtaaggaggg ggatgcctaa     540
ggctaggctt gcgactggag tgaagtcgta acaaggtagc cgtactggaa ggtgcggctg     600
gatcacctcc t                                                          611
```

<210> SEQ ID NO 24
<211> LENGTH: 22902
<212> TYPE: DNA
<213> ORGANISM: Zea Mays

<400> SEQUENCE: 24

```
attcattatt ggcccaccat tgattacaag atttagcttt tatgaatcgc tattggtttg      60
atacgaataa tggcagtcgt ttcagtttgt taaggataca gatgtatcca caattcattt     120
agagttactt aatagcctat ttcttatact atatctctat cccgtgaaat tctcaagccc     180
aaagatggat gcatatgctg tgtttcattt tgctaaatga tatcaattaa atggtatatc     240
aattctataa attggatata acaataaata aatcagaaaa attctttat tttagataga      300
agaaatgttt cttctatcta aaataaatga atgtacccct ctatccaaat ccaatttgca     360
tcgataaaat aaatccaaat tccagattct agcagtagat gaataattgc aaattttgt      420
gtgtacgaga ttagaataac ttaaaaataa ctgacataat tttttatttt tcctgaccaa     480
aaaaatacat gaaaaagaaa ggaggtagaa aaatttgttg atttatggtt aaagaagaaa     540
aacaagaaaa caggggttct gttgaatttc aagtattcag tttcactaat aagatacgga     600
gacttgcttc acatttagaa ttacacaaaa aatatttttc atcggaaaga ggtctacgaa     660
gactttgggg aaaacgtcaa agtttgctgg cttatttggt aaagaaaaat agagtacgtt     720
ataagaaatt aataagtcag ttggatattc gggagaagta atttaatcgt tctcattttt     780
ttcttatttt attagtagtc ttatagtagt attagatttt gtattttgat gagcctcgtt     840
ttgaggaatt catggaataa tccatttcca tggaataaag aataagaaca aggatatgag     900
tctatcgctt aaaagaaaag atctcatgat agtcaatatg ggcactcaac acccatcaat     960
gcatggtgtt cttcgactga ttgttactct cgatggtgaa gatgttattg attgtgaacc    1020
catattaggg tatttacaca gaggaatgga aaaaatcgcg gaaaacagaa gtattataca    1080
atacttgcct tatgtaacac gatgggatta tttagctact atgtttacag aagcaataac    1140
ggtaaatgca ccagaattct tagagaatat tcaattaccc aaaagagcca actatattag    1200
agtaattatg ttagaattga gccgtatagc ttctcatttg ttatggcttg gaccttttat    1260
ggaggatctc ggggcacaga ctccctttt ctacatttt agagagagag agaattgata    1320
tatgatctat ttgaagctgc tacaggtatg cgaatgatgc ataattactt tcgcatcgga    1380
```

```
ggagtcgctg ccgatctccc ttatggatgg atggataaat gtttagattt ctgtgattat   1440
tttttacaag gagttgttga atatcaagaa cttattacac agaatcccat tttttagaa    1500 cgagttgaag gagtcggttt tattagcgga gaagaagctg taaattgggg cttatcggga   1560
ccaatgttac gagcttctgg aatacaatgg gatcttcgta aaattgatcc ttatgagtct   1620
tacaatcaat tcgattggaa agtccaatgg caaaagaag gagattcgtt agctcgctat     1680
ttagtacgag tcggtgaaat gagggaatcc ataaaaatta ttcaacaggc tgtagagaaa   1740
attcctagag gaccttatga gaatttagaa gcccgacgct ttaagaaagc aaagaatccc   1800
gaatggaatg atttttgaata tcgattcttt ggtaaaaaac cttcgcccaa ttctgaatta   1860
tcaaagcaag agctttatgt aagagtagaa gctccaaaag gcgaattagg aatttatctg   1920
gtaggagatg atagtctttt ccctggaga tggaaaattc gtccaccggg ttttattaat     1980
ttgcaaattc ttcctcatct agttaaaaaa atgaaattgg ctgatatcat gacaatatta   2040
ggtagtatag atatcattat gggggaagtt gatcgttgaa atgataatag ataggggtaga  2100 ggtagaaact atcaattctt tttcgaaatc agaattattt aaagaaatct acgaacttat    2160
atggattcta cccattttg ccctcctact gggaatcaca atagaagtac tcgtaattgt     2220
gtggttagaa agagaaatat ccgcatcgat acaacaacgt attggtcctg aatatgctgg   2280
ccccctggga ctgcttcaag ctatagcaga tggaactaaa ctactttaaa aagaggatat   2340
cctcccatcc cgaggagata ttcctttatt tagcattggt ccctctatag cagtcatatc   2400 catttttatta agttttttag ttatccctt aggatatcgt tttgttttag ctgatcttag    2460
tattggtgtt ttttatggat tgcgatttca agtattgctc ctattggtct tctcatggca   2520
ggatatagct caaataataa atattctttt tcaggcggtc tacgagcggc tgctcaatct   2580
attagttatg aaataccatt aactttttgt gtactagcaa tatctctacg tgtgattcgt   2640
taaaatagga tcttttttcct ctaaaataca ttgaatgctt atcttccttt gcttattctg  2700
tattcgcgtt ggtaagttaa actcgatagc tatatgagtg aaacaaaaca gcttattaat   2760
ttgtagtaaa agtaaaaaat ctcatttcct acgtacaaga aaaagttca gtaaacata     2820 agcagtgtaa actcttaacc ccaaggttga gattgtttga ttagtcatca tatcttgaag   2880
cgggcaagaa taaagattc gcgatatgga attccattac tagaatattt tgagttatta    2940
ctataattta aacttataac cacaaggcaa tcgatcaaaa tttagtgagg gattaggaac   3000
actaaagtac atacaagatt agtaatgaga gaatctaaat cattagacat ttttcgtcat   3060
aaaaggaatc ataataagga cttgaaattg gtggaaatga tcaagccgta ctttcttcag   3120
attccggtct agagtatgtt cccattcact tgttaaggaa atggctatca agaacgaatt   3180 aacccctttat tctttttta agtataccc tcctagggaa agaagagtag gacaaaagat   3240
aaggaataca atacaaaaaa gatctttatt tattctttcc ttcctttatc cctattcata   3300
cagaattcct catgaactaa tgccaaattc tttccattta ttaattgcta caacgagtga   3360
tttattccaa tattaagtta ttaccgaaca aagcaaaatt atattatata aaggatgaga   3420
tcaattcgga agcgcttttt tgttattcta gcagacgtaa ttgctttggt ctaattttgg   3480
gctttccaat caattttatc ttatctaatt ctatctatgc ccagaggatg ataccgaaac   3540
gaaacaatcc tttcctttt tctgatcata gaggagccgt atgaagctaa ggtttcatgt    3600
acggttttgg aatagcggtg agaactgtga tgttatcatc gactatgatt atctaatagt   3660
tcaagtacag ttgatatagt tgaagcacag tccaaatatg gttttttggg atggaatatt    3720
```

```
tggcgtcagc ctataggttt tctagttttt ctaatttctt ctttggcaga atgtgaaaga    3780
ttaccctttg atttaccaga agcagaagaa gaattagtag caggttatca aaccgaatat    3840
tctggtatta aatatggttt attttatctt gtttcttacc taaatttatt agtttcctct    3900
ttatttgtaa ctgttctata cttaggcggg tggaatttct ctattcccta tatatccttt    3960
tttggatttt tccaaatgaa taaaataatt ggaattttgg aaatggtaat aggtatcttt    4020
attacattaa ctaaagctta tttatttctc ttcatttcta tcacaataag atggacttta    4080
cccataatga gaatggatca gttattaaat cttggatgga aatttctttt acctatttct    4140
ctgggcaatc tcttattaac aacttcttcc caactagttt cactataaat aagaatacaa    4200
taacagtaag aatattttca acacaaacgt tctctcaaac aagagaaaga aacatacctt    4260
tttcatatat agatttagaa tatgttccct atgctaactg ggttcattac ttatggtcaa    4320
caaacaatac gcgccgcaag atacattggt caaagtttca taattaccct atcccacaca    4380
aatcgtttac ctataacgat tcactaccct tatgaaaaat caattacatt ggagcgtttc    4440
ctggggcgaa tacactttga atttgataaa tgcattgctt gtgaagtatg tgttcgcgta    4500
tgcccgatag atctacccct tgtggattgg agatttgaaa aggatattaa agaaaacaa     4560 ttgcttaatt atagtattga tttcggagtt tgtatatttt gcggtaactg tgttgaatac    4620
tgtcccacaa gttgtttatc aacgactgaa gaatatgaac tttctactta tgatcgtcat    4680
gaattgaatt acaatcagat tgctttgagt cggttaccat aatgggagat tacacaattc    4740
aaacaattag aaatttgcct caaagtaaaa tagacgaaga aaaatcttgg aattcaagaa    4800
cgattacaga ttactaggta ttaggatttt ttttattaga aaaatccatt tttactaact    4860
ctaacgaaaa agaataacta ctgattaaca acttatatgt atatacaaaa aaatatccta    4920
ataccttttt ccttccttga atcttttagt tttagtcagt tcatgaaaaa ttttatacta    4980
gaaatttctt cttatccata atggatttac ctggaccaat acatgagatt cttgtgctat    5040
ttgggggatt tggtcttcta ctaggaggtc taggagtagt attacttacc aacccaatt     5100 attctgcctt ttcgctggga ttagttcttg tttgtatatc cttattctat tttttattaa    5160
attcctactt tgtagctatc gcacaacttc ttatttatgt gggagccata aatgtcttga    5220
tcatatttgt tgtaatgttt gtaaacggct cagagtggtc taaagataag aattattgga    5280
ctattggaga tgggtttact ttactccttt gtataactat tccttttca ctaatgacta     5340 ctatcccaga tacgtcgtgg catggaattc tttggactac aagatcaaac caaatagtag    5400
aacagggtct cataaataac gttcaacaaa ttgggattca tttagcaacc gatttttatc    5460
ttccatttga actcatttcc ctaattcttg tagtttcttt aataggtaat tactatggct    5520
cgacaataag aaatacttag aatgagtcaa aattcttaga atttcaaata taaataaat    5580 aactaaagaa tcacaatttt gatttagtaa aacccatcta ctgccaatac aacaaatacc    5640
ttcttttctc ttttgttgcg taattgttct attctagtta attgaatcag ttcaattctt    5700
gtcctcatat tgaaatgaat cgagattgat aaggaggtag ttaatgatgt ttgagcatgt    5760 acttttttg agtgtctatt tattttcgat tggtatctat ggattgatca caagccaaaa     5820
catggttaga gctctaatat gtcttgaact tatactaaat tcaattaatc taaatctcgt    5880 aacatttttct gatctatttg atagtcgcca attaaaagga gacattttcg caattttgtt    5940
atagcccttg cggctgctga agcagctatt ggactatcca ttctttcttc catccatcgt    6000
aacaggaaat caactcgtat caatcaatcc aattttttga ataattagac atagaatccc    6060
ctaaacaaag gggcatatat aataataaga aacattaaga tgaatagaaa tctaatctta    6120
```

```
ttttcttatt agtgtttaat aatatccttt ttttgagtag gttatttcag agtattgttt    6180
tttacttatt gaatattgca ttttttgcaat tcattgatat tgcaatttga atattgcaat   6240
aatttatatt gaaaagatga tagccaattt attggctaat tcgaattagt atgtagaatt   6300
tgtataatta taactgttga agccttaaat tcaagtctct tggctctttt cacgctttct   6360
cacaaacaga ttacgaaata tattgcatta tttgttaaag tttggataaa ctattgcttc   6420
gtctggtgtc tacaatacat ctaatttata tagtactaat ttcatttta ccagatcgaa    6480
aatttttatg ttgaaaagga aaatttagag atccaatgtc acattctgta aaaatttatg   6540
atacatgtat aggatgcact caatgtgtac gagcttgccc aacagatgta ttagaaatga   6600
taccttggga tggatgtaaa gccaagcaaa ttgcttccgc gccgagaacc gaagattgtg   6660
tgggttgtaa gagatgcgaa tccgcctgtc caacggattt ttaagtgtcc gcttttattt   6720
agggcctgaa acaacccgca gcatggctct atcttattga tacgttacaa aaaaactcca   6780
cttgaatcgt ctgattcctc tttaccgaag aagcctgtgc tcgaaataat cgagcatggg   6840
cttttctgat caaaacgtat cttgtattta ttactttatc atgagttatt ttccttggtt   6900
aacaatactt gttgttttgc cgatatttgc aggttcatta atttttcttt tacctcataa   6960
aggaaataaa atcatatact atagctattt gtttattaga attccttcta atgacttatg   7020
cattctgtta tcatttccaa ttggaggatc ctttaatcca attaaaggag gattctaaat   7080
ggatagatgt tttcgatttc cactggagat tgggaatcga tggactttca ttaggatcta   7140
ttttattgac aagatttatc actactttag ctactttagc ggcttggccg gttactcgga   7200
attcgcaatt attctatttc ctgatgctag caatgtatag tggtcaaata ggattatttt   7260
cttcatgaga cctttacttt ttttatcatg tgggagttag aattaattcc tgtttactta   7320
cttttatcca tgtggaggga agaggcgta tgtattcagc taccaagttt attttgtata   7380
ctgcaggcgg ttccattttt ttcttaattg gagttctggg tatgggatta tatggttcca   7440
atgaacccgg attagattta gaaagattga ttaatcaatc ataccctaca acattggaaa   7500
tactactgta ttttggcttc cttattgctt atgctgtcaa attgccgatt ataccttttac  7560
atacgtggtt accagatacc catggggaag cgcattacag tacatgtatg cttttagccg   7620
gaattctatt aaagatggga gcatacggat tgattcgggt caatatgaa ttgttaccgc    7680
atgctcatta tctattttcc ccttggttgg taataatagg agcggtgcaa ataatctatg   7740
cagcttcaac ttctcttggt caacgaaatt tcaaaaaaag aatagcctac tcctccgtat   7800
ctcacatggg tttcataatt ataggaattg gttccataac caacattgga ctaaatggag   7860
ctattttaca aatattatct catggattta tcggtgctac acttttttc ttggcgggaa    7920
cggacttgtg atagaatgcg tcttgtttat ctcgaagaac tggagggaat atctatccca   7980
atgccaaaaa ttttttaccat gtttagtagc ttttcagtgg cttctcttgc cttgccggga   8040
atgagcggtt tgttgcaga attagtagta ttttttggac taattactag tcctaaattt    8100
atgttaatgc caaaaatgct aattactttt gtaatggcaa taggaatgat attaactcct   8160
atttatttat tatctatgtt acgccagatg ttctatggat acaagctatt tcatgttcca   8220
atcaaaaatt ttgtagattc tggaccacgg gaactctttc ttttaatctg tatctttta    8280
ccagtaatag atctatctcg aattttcaga attagatcta tctcgaattt ttcagaatta   8340
gatcttttc gtatctttca gaattagcta tttcatgttc catctttttc agaattagat    8400
ctatctcgaa tttttgagaa cccccttgaac gtcttttcaa agggtctca aatcaaacta    8460
```

```
aaaaggaaaa aaaccgaagg ttttatgtta tgtaattatt tagatggtaa tgtaaatgaa      8520
ccgtaactat gtaaacctat tcctaacaga ttgataccaa aatagcagat ccaaattata      8580
agaaatccta tcgaagctac aagtgcggaa ttcgtaccct tccaatttgg attttttcta      8640
ctatgtaaat atattgcaaa tatggtccag gtaataaatg cccaagtttc cttaggatcc      8700
caattccaat aggatcccca tgcctcatta gcccatactg ctccacaaag aatacccacg      8760
gttaaaagag taaaccctag actaatgaca cgataactcc aagaatccaa acgctcagtt      8820
aattgatatt tgtaataatt tggaaatacg ggaaagagg tgtttttaa agcacttctt       8880 tttgcatata aatattcaat ctcactaaag aaaaatgttt taagaaaaac attttctttt     8940
agtgaaaaga atcgaaatt ctttcgaaat ctaatgatta aagagcggc ggataataag       9000 gatccacaca aaagagttgc atagcttagt aacatcatac tgacatgcat cattaaccac     9060
tgagattgta gagcaggtac tagtattgtg gattgatgca tttcagttaa aagacccgac    9120
gtggcaaagc cttgcgttaa aatagtactt ggcgtagtta ttgtgcttaa atcatttttc     9180
gagttctgta tcttaggaat agtatgaaga atatacagta tccatgaaag gaagatcaat     9240
gactcatata aattacttaa tggaaaatgt cccgaagaaa cccaacgaga gactaaaaat    9300
cctgttatag agaaaaaagt agctatcatt ccttttttctg acgaatcacg taatccccta    9360
agttcacgaa ctaataaggt tatcaaatga atcgtaatca caattgaaat ggttgagaaa     9420
gagatatgag ttagtatatg ttctaaagtt gcaaatagca taacgataag gtcccattac    9480
aaaattggaa atttcgaatt gaatccattt tctaattttt gtattctttt tcgagaatgc    9540
cgccactcgg attcgaaccg agatgcttga gcactgcttc ctaagagcag cgtgtctacc     9600
aatttcacca tggcggctaa tttaaaataa tagttaactt aaaagaataa tagttatttt     9660
atcgtgaatc gtcgagactg ggagaagcca tagaatttag gaacattaga agttcatcat     9720
tagaagttca tcattaacta caatgaaatg cattttgtat tttagaaaaa tgatagaatg      9780
aaagccttta cactcttatt aatatgatgt accagtccta aacccattta tatgggaatt    9840
ttggataaga ttaggtggag gttgtaagtc ctattgcaag aatagttact ttttataata    9900
gaatcctcgt ttttatgaga attctattat aaaaaaaagt tctttgatag gaaaagaata    9960
ctgaggacac aatataccaa aaactttttgt tctatataat gataatggag ggattcgttc    10020
taagaatatt gtaccgagga attcgacaca taaaagtaca tttattaatt aatccgaatt    10080
attcattcat attaaataat tggaatttct tttggatagt tcaattcaga ttatttcaaa    10140
atcttattat ttgtttgctt gttgcccaga aaaaccttttt ggttttggat gctcgttgcc    10200
cctagaaaat gatcttgatt ttgctaaaga ataagattgt actatggaaa aataagtctt    10260
ttttttccaa agatttttac gaatacgctt ttttgcatc gaagtacgtt ttttggaac      10320 tgccattcaa aaagggaatt actttttttct agttgtatgt gaaagacatc tattgccaca     10380
aatcaatcct tctttctgtt ttttcttagt atttatactt agatactgaa agatacttaa    10440
attctaaatt cttctttagt tcattttgtc taatgtggat aagacaagag ttttttaaga   10500
tttttattta aatcaatttc tatatcaaat atactccata tataaatata tggtatgggg    10560
gataagccct catataagag ggggagataa aagaaggta aaattcaatt caaatagtta     10620
attaagttca gaaggctatt ccataattga attccaataa aaaaaaatac ttagtctctt    10680
aaacaagaca ttctaaaact tagagaattc tagtcattag gatttccttt tatatgaaat    10740
aagcaatatt cgagaatttc ctataaatat aggttttctt tggaattcaa tcaatcaatt    10800
acgaaacaag agagctcttt tatttttaaca aaagaaata caaaaatgat tagaaagtaa    10860
```

```
aattattcaa tcttttttg tattttaata aatatttttt tttactaata actagatacc    10920
gaaattcttt gattcactt ttgaatttaa gtaactaaac ccattctaaa ttttggaata    10980
ttttaatgag agaaattaga aaaattcata attccagtat ttttattt tcttattttg    11040
ttttttaat tcctttagaa agagataaga ataggtttgg tgaatcggaa acaatttat    11100
tttatagaaa aattgaacta taaatttaaa ctaaaaattg ctatttcttt tcttatggaa    11160
catacatatc aatatgcctg gtaattcct cttctcccac ttccagttat tatgtcaatg    11220
ggatttggac tttttcttat tcctacagca acaaaaaatc ttcgtcggat atgggctttt    11280
cctagtattt tactcttaag tatagctatg gtattctcac ttcacctgtc tattcaacaa    11340
ataaatggaa gttctatcta tcaatatcta tggtcttgga ccatcaataa tgattttcc    11400
ttagaatttg gatacttggt cgacccctt acgtctatta tgttaatact aattactact    11460
gtaggaatct tagttcttat ttatagtgac gattatatgt ctcacgatga aggatatttg    11520
agatttttg tttatataag tttttttaat acttccatgt taggattggt tactagttcc    11580
aatttgatac aaatttattt ttttgggaa cttgtcggaa tgtgttccta tttattgata    11640
ggcttttggt ttacgcggcc aattgcagcg agtgcttgtc aaaaagcttt tgtaactaat    11700
cgtgtagggg attttggtct gttattagga attttaggtt ttttttggat aacgggtagt    11760
ttggagtttc gggatttgtt caaaatagct aataactgga ttcctaataa tgggattaat    11820
tccttactta ctactttgtg tgcttttta ttattccttg gtgcagttgc aaaatctgca    11880
caatttcctc ttcacgtatg gttacctgat gctatggaag gacccactcc tatttcggct    11940
cttatacacg cagcaactat ggttgctgcg gggatttttc ttctagctag acttcttcct    12000
cttttcatat ccctaccctg gataatgagt ttcatttctt taataggtac aataacactc    12060
ttcttaggag ccactttagc tcttgctcag agagatatta aagaagctt agcctattct    12120
acaatgtctc aattgggta tatgatgtta gctctaggta taggttctta tcaagctgct    12180
ttattccatt tgatcactca tgcttattcg aaagctttat tgttcttagg atccggatcc    12240
gttattcatt caatggaacc tcttgttgga tattcaccag ataaaagtca gaatatggtt    12300
cttatgggtg gtttaagaaa atacgttcca attacaagaa ctactttttt atgtggtaca    12360
ctttctcttt gtggtattcc acctcttgct tgcttctggt ccaaagatga aatccttagt    12420
aatagttggt tgtattcacc ctttttgga ataatagcct ttttactgc aggattaact    12480
gcatttttata tgtttcggat atatttactt actttgatg ggtatttgcg tgttcatttt    12540
caaaattaca gtagtactaa agaaggttcg ttgtattcaa tatccttatg gggaaaaagt    12600
atatccaaag gagtcaatag ggattttgtt ttatcaacaa tgaagagtgg agtttcttt    12660
ttttcacaaa ataaccaaa aattcctgct aatacaagaa ataagatagg atcctttagt    12720
actcccttg gggctaaaa tacttttgtc tatcctcatg aaacgggaaa tactatgcta    12780
tttcctcttc ttatatact acttttact ttgttcattg gatccatagg aatccatttt    12840
gataatggag taaagataa tagaatattg gagttaacca tattatcaaa gtggctaact    12900
ccttcaataa acttgttcca ggaaaattct aattcttcca taaattcata tgaatttctc    12960
actaatgcaa tttcttctgt aagtttagca atttttggtc tattcatagc atatatcttt    13020
tatggatctg cttattcttt ttttcagaat ttgaattttc aaaattccct tgtaaaaaag    13080
aatccaaaaa agagcttttt ggatgaagta aaaaaaaga tatacagctg gtcatataat    13140
cgtggttata tagatttttt ctatactagg gttttatcc taggtataag aagattagcc    13200
```

```
gaactaacgc attttttgta taaaggtgtc attgatggaa ttaccaatgg agtaggtctt   13260
gctggttttt gtataggaga agaaatcaaa tatgtagggg gagggcgaat atcgtcttat   13320
ctattctttt ttttatgtta tgtatccttg ttcttattct ttattccatg aaaatggatt   13380
attccatgaa ttcctcaaaa cgaggctcat caaaatgcaa aatctaagac tactataaga   13440
ctactaataa aataagaaaa aaatgagaac gattaaatta cttctcccga atatccaact   13500
gacttattaa tttcttataa cgtactctat ttttctttgc caaataagcc agcaaacgtt   13560
gacgttttcc caaaagtctt cgtagacctc tttccgatga aaaatctttt ttgtgtaatt   13620
ctaaatgtga agcaagtctc cgtatcttat tggtgaaact gaatacttga aattcaacag   13680 aaccctgtt tcttgttttt tcttctttaa ccataaatca acaattttt ctacctcctt    13740 tcttttcat gtattttct gatcaggaaa aataaaaat tatgtcagtt atttttaagt      13800
tattctaatc tcgtacacac aaaaatttgc aattattcat ctactgctgg aatctggaat   13860
ttggatttat tttatcgatg caaattggat ttggatagaa gggtacattc ttttatttta   13920
gatagaagaa acatttcttc tatctaaaat aaaagaattt tgctgattta tttattgcta   13980
tatccaattt atagaattga tataccattt aattgatatc atttagcaaa atgaaacaca   14040
gcatatgcat ccatctttgg gctcgagaat ttcacgggga agagatatag tataagaaat   14100
aggctattaa gtaactctaa atgaattgtg gatacatctg tatccttaac atactgaaac   14160
gactgccatt attcgtatca aaccaatagc gattcataaa agctaaatct tgtaatcaat   14220
ggtgggccaa taatgaattt ttttgcatat gtattaagac gcttggtctg atttcgaaat   14280
tgtccagagt tttttatgtt gttttcattg caaaatgatg gatctccttc cgtaactttc   14340
caattacgag tacgagaatt gaaagacatg aaaattctca attctctacg gcgtctagga   14400
gatggatcga atattttcag gaacaagaaa atcagaagaa tcttttttctc tattcactac   14460 cattccgcgt cttcgacttc tattagtttc ttttcttctt taatgcaata gctatagttt   14520
gatatagaat ccatttctca aagtaatgga aaccattctc ttataggaaa tggttcgaaa   14580
atcgctattc caccttttag gtttaggtat cgtgaaaagt gatacctgtg aagatcgtgc   14640
atttcagtca cattcagatc cgttttttcga gtccatgata taaccaaatt ggatggatct   14700
tccacccgtt tagctaagaa agaatagatg cagaggtgga taatagatcg atatgaagat   14760
catgagctgc cccataatga aaccgccagt agtcgcgaat atctccttct tccctaaccc   14820
aagattggag aaagaagatc taagagggac ctatggagaa tgtggtcaga aatccataat   14880
agagtccgac cacaacgacc gaattaatta tcctcatcga gaaacttaga ctactttaga   14940
ctacttaagt agaaaagatt tgaaaatcat ggcatgggtc tccttttttt ctttctttag   15000
agttttctat atgcacaatt tctcgatgtt tcgatgagaa tttcttgact ttccatatat   15060
agaaagagat agactataaa tgacatctct tatgtcaata agaccaaagg aatggatatt   15120
aaatgatagg aagtgctaag aagtgaaata gaatgaaata gagccacttt gggcttccct   15180
atgaaatgag gcatggaacg gagccactac gaagaaattc cggagttac gaaagaagct    15240 tcggactcat attgttcacg ggttgagagc gggagttgaa ctctaggagg tcgaatctcc   15300
ccttgttcct cagtagctca gtggtagagc ggtcggctgt taactgactg gtcgtaggtt   15360
cgaatcctac ttggggagat tgattcatt ctttaatgta agaataaaga attgaattaa    15420
aaggcttgct ttgaccctta ggagtaggta acccgttcgc tatccttgtt tctattgcat   15480
tctgtctcat cgtatcacat tctgttctac gattccactt cgacaaaagg aaagagcata   15540
cccaagttca atagctttac gtccgctatt ccgatcatga ttttcctacc ctcagggaga   15600
```

```
aagtaaaggt ccttccccct ttggaaggct gtgggcgagg agggattcga accccgaca   15660 ccgtggttcg tagccacgtg ctctaatcct ctgagctaca ggcccacccc gtctccactg   15720
gatctcttcc cggggatacc ccccaaaagg aaccttcttc tcctcagcca tttcatttcg   15780
ggttaagaag atgggaaagc gcctttctct ctataagaac agtgcgttct gaggtgtgaa   15840
gtgggagaga ggggatgatt gaggttttga ataagacgac ctttgcgttt tggatttgga   15900 tcttttcgt atttcaaaat agtgaaaaag tcaataaga ggtgttaagc ttttatcat     15960 tctggcatcg agctattttg ccgcaggacc tcccctacag tatcgtcacc gcagtagagt   16020
ttaaccacca aattcgggat ggattggtgt ggttcctcta cgcctaggac accagaatat   16080
cgaaccatga acgagaaaag gcatgagaga aatattggct agtaattgtg aagtcccaat   16140
tcttaactgg aagggacacc aaaggactct gccctccctc tctatttatc caagagatgg   16200
aagggcagag cttttttttg gttttttcat cttttcttt catcaaagag ttgaacaatg    16260
aagatagatg gcaagtgcct gatcgatttg atcaggtcgt gtaggaacaa ggttcaaatc   16320
gttcgttcgt taggatgcct cagctgcata catcactgca cttccacttg acacctattt   16380
aaacggctcg tctcgccgct accttatcct atttccatac ttctgtcgct ccatcccgt    16440 atgggtggag aacccgtcgc tgtctcggct gtgctaccgg aggctctagg gaagtcggag   16500
gagagagcac tcatcttggg gtgggcttac tacttatatg ctttcagcag ttatcctctc   16560
cacacttggc tacccagcgt ttaccgtagg cacgataact ggtacaccag aggtgcgtcc   16620
ttcccggtcc tctcgtacta gggaaaggtc ctctcaatgc tctaacgccc acaccggata   16680
tggaccgaac tgtctcacga cgttctgaac ccagctcacg taccgcatta atgggcgaac   16740
agcccaaccc ttggaaccac ctacagctcc aggtggcgaa gagccgacat cgaggtgcca   16800
aaccttcccg tcgatgtgga ctcttgggga agatcagcct gttatcccta gagtaacttt   16860
tatccgttga gcgacggccc ttccactcgg caccgtcgga tcactaaggc cgactttcgt   16920
ctctgctcga cgggtgagtc ttgcagtcaa gctcccttct gcctttgcac tcgaggacca   16980
atgtccgtct ggcccgagga aacctttgca cgcctccgtt accttttggg aggcctacgc   17040
cccatagaaa ctgtctacct gagactgtcc cttggcccgc gggtctgaca caaggttaga   17100
atccgagctc ttccagagtg gtatctcact gatggctcgg gccccccgg aagggggcct    17160 tcttcgcctt ccacctaagc tgcgcaggaa agcccaaag ccaatcccag ggaacagtaa     17220
agcttcatag ggtctttctg tccaggtgca ggtagtccgc atcttcacag acatgtctat   17280
ttcaccgagc ctctctccga gacagtgccc agatcgttac gcctttcgtg cgggtcggaa   17340
cttacccgac aaggaatttc gctaccttag gaccgttata gttacggccg ccgttcaccg   17400
gggcttcggt cgccggcttc cctgtcatca gttcaccaac ttccttgacc ttccggcact   17460
gggcaggcgt cagcccccat acatggtctt acgactttgc ggagacctgt gtttttggta   17520
aacagtcgcc cgggcctggt cactgcgacc ccctttttgcg aggggcacc ccttctcccg    17580 aagttacggg gctattttgc cgagttcctt agagagagtt gtctcgcgcc cctaggtatt   17640
ctctacctac ccacctgtgt cggtttcggg tacaggtacc cttttgttga aggtcgttcg   17700
agcttttcct gggagtatgg catgggttac atacttcagc gccgtagcgc ctggtatgag   17760
cctcgtggag aagcaatggc tagtccacgg ggctcatact tcagcgctgc agcgcttggt   17820
actcggacct cggctcgagg cattttctct acccccttctt acccctgaaaa agcagggtca   17880 ccttgtgtcc ttaaacctat aaccatcttt cggctaacct agcctcctcc gtccctccgt   17940
```

-continued

```
accaacaagg ggtagtacag gaatattgac ctgttgtcca tcgactacgc ctttcggcct    18000
gatcttaggc cctgactcac cctccgtgga cgaaccttgc ggaggaaacc ttgggttttc    18060
ggggcattgg attctcacca atgttttcgt tactcaagcc gacattctcg cttccgcttc    18120
gtcgaccccc gctttcgcgt ttgcttccct ctaaggcgga acgctcccct accgatgcat    18180
tttgacatcc cacagcttcg gcagatcgct tagccccgtt catcttcagc gcaagggcgc    18240
tcgatcagtg agctattacg cactctttaa agggtggctg cttctaggca aacctcctgg    18300
ctgtctttgc accccccacct cctttatcac tgagcggtca tttaggggcc ttagctggtg    18360
atccgggctg tttccctctc gacgatgaag cttatccccc atcgtctcac tggccgacct    18420 tgaccccctgt tattttttggg tcatatctag tattcagagt ttgcctcgat ttggtaccgc    18480
tcgcgcagcc cgcaccgaaa cagtgcttta cccctagatg tccagtcaac tgctgcgcct    18540
caacgcattt cggggagaac cagctagctc tgggttcgag tggcatttca ccctaaccaa    18600
caactcatcc gctgattctt caacatcagt cggttcggac ctctgcttag tttcatccaa    18660
gcttcatcct ggtcatggat agatcaccca ggttcgggtc cataagcagt gacaatcgcc    18720
ctatgaagac tcgctttcgc tacggctccg gtgggttcca ttcccttaac caagccactg    18780
cctatgagtc gccggctcat tcttcaacag gcacgcggtc agagatcact ttccccctccc    18840 actgcttggg agctcagcac ggtttcacgt tctatttcac tacccactgg gggttctttt    18900
cacctttccc tcacggtact acttcgctat cggtcaccca ggagtattta gccttgcaag    18960
gtggtccttg ctgattcaca cgggattcca cgtgccccat gctactcggg tcagagcgta    19020
agctagtgat gctttcggct actggacttt agccatctag ggtgcggcac tcaaccgctt    19080
cgcctagcag cacaacgctt gtattgctct cccacaaccc cgttttcacg gtttaggctg    19140
ctcccatttc gctcgccgct actacgggaa tcgcttttgc tttcttttcc tctggctact    19200
aagatgtttc agttcgccag gttgtctctt gcctgctcat ggattcagca ggcagttcaa    19260
aaggttgacc tatttgggaa tctccggatc tatgcttatt ttcaactccc cgaagcattt    19320
cgtcgcttgc tacgcccttc ctcgtctctg ggtgcctagg tatccaccgc aagcctttcc    19380
tcttttgaac ctcgccatta acgttaaggc tatgccatcc taaggtgcta ctaaatggaa    19440
ggatcttatc aacgtccatg aatgcgaaat catagatcga actgacgaat tggcaacctt    19500
cggtgctatc atagtatccg ctaagttcac gggctggaga taagcggact cgaaccgctg    19560
acatccgcca cagggtaaac caccgcctct caggcctccc cgacgggttc taccatagag    19620
gacaacgata ggcaataact cccccccgaa cacagcttac aactttcatc gtactgtgct    19680
ctccaaagag caactcttct caaaatccca aaacaaaagg tgctgagttg gaatcccatt    19740
ctaaggattc ttgtggttcc ggggaatcca gctacaggag aaccaggaac ggggagctct    19800
cccctttttc cgcccgactc tttgatctta acttaagaat gctggtttta agaacgagtg    19860
attgcccttc tccgaccctt actgcccaac cggagagcgg acggctaatg tgttccactt    19920
attgaacagg atctatggtc ggtccgtgac ccctggacgc cgaaggcgtc cttggggtga    19980
tctcgtagtt cctacggggt ggagacaatg gggtcggtcc atggattttc cttccttttg    20040
ccacatttcg ctcaaagggt tgaagggaga tagtgcatca agctattcgc aagggccaac    20100
ttgatcctct tccccaggga tcccagatga gggaagccta ggagagccgc cgactccaac    20160
tatcgtccat gtacgatcca tactagatct gaccaactgc ccatcctacc tcctctacct    20220
ttttgacagc ccatctttt gtctcagtag agtcttcag tggcatgttt cagtcctctt    20280
ccccattact tagaaaaagt gagccaccgg ttcaggtaca agatactatc attaccgcct    20340
```

```
ggacaattag acagccaacc cgtaatcgca acgacccaat tgcaagagcg gagctctacc   20400
aactgagcta tatccccccc gagccaagtg gagtatgcat gaaagagtca gatgcttctt   20460
ctattctttt ccctggcgca gctgggccat cctggacttg aaccagagac ctcgcccgtg   20520
aagtaaatca tcgcccctac gatccaacca attgggagag aatcaataga ctccttttcg   20580
ggagcgattc atccttcccg aacgcagcat acaactcccc gttgtactgc gctcttcaag   20640
tgtgcttctt ccccttctc cccttacca cggcaagtcc ttgggaaata actccgatgg   20700
gcagaaaaaa aagggggtta agagaccctc ctggcccaac cctagacact ctaagatcct   20760
ttttcaaacc tgctctgctc ccatttcgag tcaagagata gataaatagc cacatcccat   20820
tgcactgatc gggggcgctc gtagtgactt aggggggtcga agaccaagaa gtggcttatt   20880
tataccaagc attcctctta tggctagatc caatctcctg gtccctgcag aaaggaaaaa   20940
gaatttcacg ttcttccttt caggaaggga ggattaggga agtcctattg attactgctt   21000
tctccagacc gccgggaaaa gcatgaaaaa aaggctcgaa tggtacgatc cctccgtcac   21060
cccagaatga aagggggtgat ctcgtagttc ttggtctgtg aagatgcgtt gttaggtgct   21120
ccattttccc attgaggacg aacctcaacc tgtgctcgag agatagctct ccatacactg   21180
ataagggatg tatggattct cgagaagaga ggagccgcgg tggcccccc ccggaccgcc   21240 cggatcccac gagtgaatag aaagttcgat ctacatggga tctcacctga atcgccccat   21300
ctatcctcct gaggagaagt ttgtttggtt tcaaactccg attcaaacag gaggagtacg   21360
ccatgctaat gtgccttgga tgatccacat cttcgggtca ggcgctgatg agcacattga   21420
actatccatg tggctgagag ccctcacagc ccaggcacaa cgacgcaatt atcaggggcg   21480
cgctctacca ctgagctaat agcccgtcgc gcgggcctcc caagggagg cctgctacgc   21540 caaaagcgag aaaactcca tcccttcct tttgacatcc ccatgccgcc acacgggggg   21600
acatggggac gtcaaaaagg ggatcctatc actatcaact aatttgttcc gacctaggat   21660
aataagctca tgagcttggt cttacttcac cctaaacgaa agaagacttc catatccaag   21720
tttagctcag acgtagctgc cttctttttg ggcgtgaagc agtgtcaaac caaaataccc   21780
aataagcata agcattagct ctccctgaaa aggaggtgat ccagccgcac cttccagtac   21840
ggctaccttg ttacgacttc actccagtcg caagcctagc cttaggcatc cccctcctta   21900
cggttaaggg taatgacttc aaacctggcc agctcctata gtgtgacggg cggtgtgtac   21960
aaggcccggg aacggattca ccgccgtatg gctgaccggc gattactagc gattcctgct   22020
tcatgcaggc gagttgcagc ctgcaatccg aactgaggac gggttttttgg agttagctca   22080 ccctcgcgag atcgcgaccc tttgtcccgc ccattgtagc acgtgtgtcg cccagggcat   22140
aaggggcatg atgacttggc ctcatcctct ccttcctccg gcttaacacc ggcggtctgt   22200
tcagggttcc aaactcatag tggcaactaa acacgagggt tgcgctcgtt gcgagactta   22260
acccaacacc ttacggcacg agctgacgac agccatgcac cacctgtgtc cgcgttcccg   22320
agggcacccc tctctttcaa gaggattcgc ggcatgtcaa gccctggtaa ggttcttcgc   22380
tttgcatcga attaaaccac atgctccacc gcttgtgcgg gccccgtca attcctttga   22440 gtttcattct tgcgaacgta ctccccaggc gggatactta acgcgttagc tacagcactg   22500
cacgggtcga gtcgcacagc acctagtatc catcgtttac ggctaggact actggggtct   22560
ctaatcccat ttgctcccct agctttcgtc tctcagtgtc agtgtcggcc cagcagagtg   22620
cttccgccgt tggtgttctt tccgatctca atgcatttca ccgctccacc ggaaattccc   22680
```

```
tctgccccta ccgtactcca gcttggtagt ttccaccgcc tgtccagggt tgagccctgg     22740
gatttgacgg cggacttgaa aagccaccta cagacgcttt acgcccaatc attccggata     22800
acgcttgcat cctctgtctt accgcggctg ctggcacaga gttagccgat gcttattcct     22860
cagataccgt cattgtttct ctccgagaa aagaagttga cg                         22902
```

<210> SEQ ID NO 25
<211> LENGTH: 1029
<212> TYPE: DNA
<213> ORGANISM: Zea Mays

<400> SEQUENCE: 25

```
atggatttac ctggaccaat acatgagatt cttgtgctat ttgggggatt tggtcttcta      60
ctaggaggtc taggagtagt attacttacc aacccaattt attctgcctt ttcgctggga     120
ttagttcttg tttgtatatc cttattctat tttttattaa attcctactt tgtagctatc     180
gcacaacttc ttatttatgt gggagccata aatgtcttga tcatatttgt tgtaatgttt     240
gtaaacggct cagagtggtc taaagataag aattattgga ctattggaga tgggtttact     300
ttactccttt gtataactat tccttttca ctaatgacta ctatcccaga tacgtcgtgg     360
catggaattc tttggactac aagatcaaac caaatagtag aacagggtct cataaataac     420
gttcaacaaa ttgggattca tttagcaacc gatttttatc ttccatttga actcatttcc     480
ctaattcttg tagtttcttt aataggaatc catttgata atggagtaaa agataataga     540
atattggagt taaccatatt atcaaagtgg ctaactcctt caataaactt gttccaggaa     600
aattctaatt cttccataaa ttcatatgaa tttctcacta atgcaatttc ttcttcaagc     660
tcccttctgc ctttgcactc gaggaccaat gtccgtctgg cccgaggaaa cctttgcacg     720
cctccgttac cttttgggag cctacgcccc catagaaact gtctacctga gactgtccct     780
tggcccgcgg gtctgacaca aggtaccctt tgttgaagg tcgttcgagc ttttcctggg     840
agtatggcat gggttacata cttcagcgcc gtagcgcctg gtatgagcct cgtggagaag     900
caatggctag tccacggggc tcatacttca gcgctgcagc gcttggtact cggacctcgg     960
ctcgaggcat tttctctacc ccttcttacc ctgaaaaagc agggtcacct tgtgtcctta    1020
aacctataa                                                            1029
```

<210> SEQ ID NO 26
<211> LENGTH: 342
<212> TYPE: PRT
<213> ORGANISM: Zea Mays

<400> SEQUENCE: 26

```
Met Asp Leu Pro Gly Pro Ile His Glu Ile Leu Val Leu Phe Gly Gly
1               5                   10                  15

Phe Gly Leu Leu Leu Gly Gly Leu Gly Val Val Leu Leu Thr Asn Pro
            20                  25                  30

Ile Tyr Ser Ala Phe Ser Leu Gly Leu Val Leu Val Cys Ile Ser Leu
        35                  40                  45

Phe Tyr Phe Leu Leu Asn Ser Tyr Phe Val Ala Ile Ala Gln Leu Leu
    50                  55                  60

Ile Tyr Val Gly Ala Ile Asn Val Leu Ile Ile Phe Val Val Met Phe
65                  70                  75                  80

Val Asn Gly Ser Glu Trp Ser Lys Asp Lys Asn Tyr Trp Thr Ile Gly
                85                  90                  95
```

```
Asp Gly Phe Thr Leu Leu Cys Ile Thr Ile Pro Phe Ser Leu Met
            100                 105                 110

Thr Thr Ile Pro Asp Thr Ser Trp His Gly Ile Leu Trp Thr Thr Arg
        115                 120                 125

Ser Asn Gln Ile Val Glu Gln Gly Leu Ile Asn Val Gln Gln Ile
    130                 135                 140

Gly Ile His Leu Ala Thr Asp Phe Tyr Leu Pro Phe Glu Leu Ile Ser
145                 150                 155                 160

Leu Ile Leu Val Val Ser Leu Ile Gly Ile His Phe Asn Asp Asn Gly Val
                165                 170                 175

Lys Asp Asn Arg Ile Leu Glu Leu Thr Ile Leu Ser Lys Trp Leu Thr
                180                 185                 190

Pro Ser Ile Asn Leu Phe Gln Glu Asn Ser Asn Ser Ile Asn Ser
            195                 200                 205

Tyr Glu Phe Leu Thr Asn Ala Ile Ser Ser Ser Ser Leu Leu Pro
    210                 215                 220

Leu His Ser Arg Thr Asn Val Arg Leu Ala Arg Gly Asn Leu Cys Thr
225                 230                 235                 240

Pro Pro Leu Pro Phe Gly Arg Pro Thr Pro His Arg Asn Cys Leu Pro
                245                 250                 255

Glu Thr Val Pro Trp Pro Ala Gly Leu Thr Gln Gly Thr Leu Leu Leu
            260                 265                 270

Lys Val Val Arg Ala Phe Pro Gly Ser Met Ala Trp Val Thr Tyr Phe
                275                 280                 285

Ser Ala Val Ala Pro Gly Met Ser Leu Val Glu Lys Gln Trp Leu Val
            290                 295                 300

His Gly Ala His Thr Ser Ala Leu Gln Arg Leu Val Leu Gly Pro Arg
305                 310                 315                 320

Leu Glu Ala Phe Ser Leu Pro Leu Leu Thr Leu Lys Lys Gln Gly His
                325                 330                 335

Leu Val Ser Leu Asn Leu
            340

<210> SEQ ID NO 27
<211> LENGTH: 21
<212> TYPE: DNA
<213> ORGANISM: Zea Mays

<400> SEQUENCE: 27
atgacgagtt ttcacgtccg a                                       21

<210> SEQ ID NO 28
<211> LENGTH: 22
<212> TYPE: DNA
<213> ORGANISM: Zea Mays

<400> SEQUENCE: 28
cgttcacgcg atttttcaag tg                                      22
```

METHODS OF IDENTIFYING, SELECTING, AND PRODUCING DISEASE RESISTANT CROPS

CROSS REFERENCE TO RELATED APPLICATIONS

This application claims priority to Chinese Patent Application Nos. 202010042670.5, filed on Jan. 15, 2020 and 202011200759.6, filed on Oct. 30, 2020, the disclosures of which are hereby expressly incorporated by reference in their entirety.

REFERENCE TO SEQUENCE LISTING SUBMITTED ELECTRONICALLY

A sequence listing having the file name "RTS22658A_SeqList.txt" created on Oct. 15, 2020 and having a size of 114 kilobytes is filed in computer readable form concurrently with the specification. The sequence listing is part of the specification and is herein incorporated by reference in its entirety.

FIELD

The field is related to plant breeding and methods of identifying and selecting plants with disease resistance. Provided are methods to identify novel genes that encode proteins providing plant disease resistance and uses thereof. These disease resistant genes are useful in the production of resistant plants through breeding, transgenic modification, or genome editing.

BACKGROUND

Corn southern rust (SCR), a fungal disease caused by *Puccinia polysora* Underw, is a major disease in the tropical regions and southern part of the US and China. If SCR reaches the temperate regions (e.g. US Midwest) at critical points in the growing season and if conditions are favorable for rust development, disease intensity can reach epidemic levels very quickly, resulting in severe yield losses. Temperate maize germplasm is in general susceptible to SCR. The identification and utilization of resistance lines and QTL in breeding programs to develop varieties resistance to SCR represent a cost-effective way in controlling SCR. Alternatively, varieties carrying genes responsible to SCR resistance may be developed by transgenic or genome editing technologies. Identification of resistance QTL and genes would accelerate the development of products resistance to SCR. Resistance lines (e.g. Brewbaker, J. L., et al. "General resistance in maize to southern rust (*Puccinia polysora* Underw.)." Crop science 51, no. 4 (2011): 1393-1409) or QTL (e.g. Jines, M. P., et al. "Mapping resistance to Southern rust in a tropical by temperate maize recombinant inbred topcross population." Theoretical and Applied Genetics 114, no. 4 (2007): 659-667. Zhang, Y., et al. "Mapping of southern corn rust-resistant genes in the W2D inbred line of maize (*Zea mays* L.)." Molecular breeding 25, no. 3 (2010): 433-439. Zhou C J, et al. (2007) Characterization and fine mapping of RppQ, a resistance gene to southern corn rust in maize Mol Genet Genomics 278:723-728. Holland, J. B., et al. "Inheritance of resistance to southern corn rust in tropical-by-corn-belt maize populations." Theoretical and Applied Genetics 96, no. 2 (1998): 232-241.) have been identified. However, none of the causal genes responsible for SCR resistance have been identified and characterized. There is a continuous need for disease-resistant plants and methods to find disease resistant genes.

SUMMARY

Compositions and methods useful in identifying and selecting plant disease resistance genes, or "R genes," are provided herein. The compositions and methods are useful in selecting disease resistant plants, creating transgenic resistant plants, and/or creating resistant genome edited plants. Plants having newly conferred or enhanced resistance various plant diseases as compared to control plants are also provided herein. In some embodiments, the compositions and methods are useful in selecting disease resistant corn plants, including corn southern rust (SCR) disease resistant plants, creating transgenic disease resistant plants, and/or creating disease resistant genome edited plants.

A disease resistant plant may be crossed to a second plant in order to obtain a progeny plant that has the resistant gene allele. The disease resistance may be newly conferred or enhanced relative to a control plant that does not have the favorable allele. The R gene allele may be further refined to a chromosomal interval defined by and including defined markers. In some embodiments, the methods for identifying and/or selecting plants having disease resistance are presented. In these methods, DNA of a plant is analyzed for the presence of a resistant gene allele on chromosome 7 that is associated with disease resistance, wherein said resistant gene allele comprises a sequence having at least 95% identity to SEQ ID NOs: 1-10 or 13-16; and a plant is identified and/or selected as having disease resistance if said resistant gene allele is detected. In some embodiments, the methods for identifying and/or selecting plants having disease resistance comprise detecting or selecting a genomic region comprising any one of SEQ ID NOs: 4-6. The disease resistance may be newly conferred or enhanced relative to a control plant that does not have the favorable allele. In a further embodiment, the disease resistant region comprises a gene encoding a ZmMM1 polypeptide that confers or enhances disease resistance (the "ZmMM1 gene"). In some embodiments, the ZmMM1 polypeptide comprises the amino acid sequence as set forth in any one of SEQ ID NOs: 1-3.

In another embodiment, methods of identifying and/or selecting plants with disease resistance are provided in which one or more marker alleles linked to and associated with any of SEQ ID NO: 1-10 or 13-16 are detected in a plant, and a plant having the one or more marker alleles is selected. The one or more marker alleles may be linked by 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM or less on a single meiosis based genetic map. The selected plant may be crossed to a second plant to obtain a progeny plant that has one or more marker alleles linked to and associated with any of SEQ ID NO: 1-10 or 13-16.

In another embodiment, methods of introgressing a gene allele associated with disease resistance are presented herein. In these methods, a population of plants is screened with one or more markers to determine if any of the plants has a gene allele associated with disease resistance, and at least one plant that has the gene allele associated with disease resistance is selected from the population. The gene allele comprises a sequence having at least 95% identity to SEQ ID NOs: 1-10 or 13-16.

In some embodiments, introgression of disease resistant genes from resistant to susceptible lines may be achieved either by marker-assisted trait introgression, transgenic, or genome editing approaches.

Embodiments include an isolated polynucleotide comprising a nucleotide sequence encoding a ZmMM1 polypeptide capable of conferring disease resistance, wherein the ZmMM1 polypeptide has an amino acid sequence of at least 50%, at least 75%, at least 80%, at least 85%, at least 90%, at least 95% identity, at least 96% identity, at least 97% identity, at least 98% identity, or at least 99% identity when compared to any one of SEQ ID NOs: 1-3. In another embodiment, an isolated polynucleotide comprises a nucleotide sequence encoding a ZmMM1 polypeptide capable of conferring resistance, wherein the ZmMM1 polypeptide has an amino acid sequence of at least 50%, at least 75%, at least 80%, at least 85%, at least 90%, and at least 95% identity, when compared to any one of SEQ ID NOs: 1-3.

Additional embodiments of the present disclosure include a vector comprising a polynucleotide of the disclosure, such as SEQ ID NO: 4-10, or a recombinant DNA construct comprising a polynucleotide disclosed herein operably linked to at least one regulatory sequence. A plant cell, as well as a plant, each comprising the recombinant DNA construct of an embodiment disclosed herein, and a seed comprising the recombinant DNA construct are also embodied.

In some embodiments, the compositions and methods relate to a modified plant having increased resistance to a disease, wherein the allele causing the increased disease resistance comprises a nucleotide sequence encoding a ZmMM1 resistance gene, wherein the ZmMM1 resistance gene is at least 50%, at least 75%, at least 80%, at least 85%, at least 90%, and at least 95% identity, at least 96% identity, at least 97% identity, at least 98% identity, or at least 99% identity to the sequence set forth in SEQ ID NO: 4-10. In some embodiments, down-regulation in maize of ZmMT1 (SEQ ID NO: 20 and 21), ZmMT2 (SEQ ID NO: 23), ZmMT3 or ZmMT4 (SEQ ID NO: 25) provides enhanced the resistance. Downregulation may be induced through editing or transgenic means, including RNAi knockdown.

The methods embodied by the present disclosure relate to a method for transforming a host cell, including a plant cell, comprising transforming the host cell with the polynucleotide of an embodiment of the present disclosure; a method for producing a plant comprising transforming a plant cell with the recombinant DNA construct of an embodiment of the present disclosure and regenerating a plant from the transformed plant cell, and methods of conferring or enhancing disease resistance, comprising transforming a plant with the recombinant DNA construct disclosed herein.

Methods of altering the level of expression of a protein capable of conferring disease resistance in a plant or plant cell comprising (a) transforming a plant cell with a recombinant DNA construct disclosed herein and (b) growing the transformed plant cell under conditions that are suitable for expression of the recombinant DNA construct wherein expression of the recombinant DNA construct results in production of altered levels of a protein capable of conferring disease resistance in the transformed host are also embodied.

Plants identified and/or selected using any of the methods presented above are also provided.

DESCRIPTION OF SEQUENCES

Figure 1:
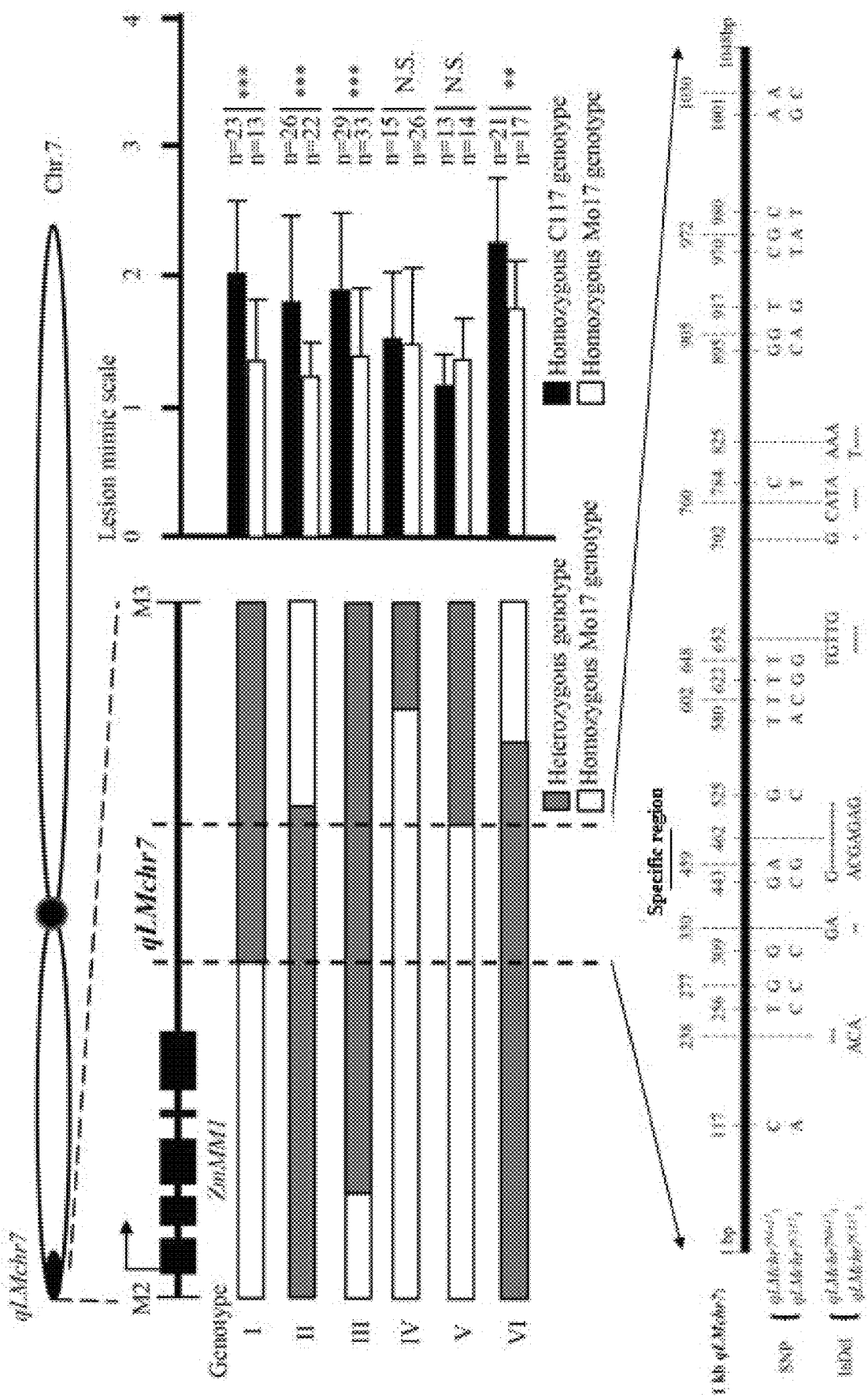
FIG. 1 shows a 5 kb interval fine mapped on chromosome 7 flanked markers M2 (SEQ ID NOs: 27 and 28) and M3 (SEQ ID NOs: 11 and 12) as well as the 20 SNPs and 7 indels between C117 and Mo17 within the 1 kb qLMchr7 region.

| SEQ ID NO: | Sequence name |
|---|---|
| 1 | ZmMM1 amino acid sequence - B73 |
| 2 | ZmMM1 amino acid sequence - Mo17 |
| 3 | ZmMM1 amino acid sequence - C117 |
| 4 | ZmMM1 genomic DNA sequence - Mo17 |
| 5 | ZmMM1 genomic DNA sequence - C117 |
| 6 | ZmMM1 genomic DNA sequence - B73 |
| 7 | ZmMM1 cDNA sequence - B73 |
| 8 | ZmMM1 cDNA sequence - Mo17 |
| 9 | ZmMM1 cDNA sequence - C117 |
| 10 | Resistant allele (C117)-specific sequence (define resistance haplotype, for molecular breeding) |
| 11 | Primer 1 (for amplifying resistance allele-specific fragment) |
| 12 | Primer 2 (for amplifying resistance allele-specific fragment) |
| 13 | Expression regulatory element from ZmMM1 3' UTR - Mo17 |
| 14 | Expression regulatory element from ZmMM1 3' UTR - C117 |
| 15 | Specific region with causal variations within the expression regulatory element - Mo17 |
| 16 | Specific region with causal variations within the expression regulatory element - C117 |
| 17 | ZmMT3 genomic sequence |
| 18 | ZmMT3 cDNA sequence |
| 19 | ZmMT1 genomic sequences (including ZmMT1-1 and ZmMt2) |
| 20 | ZmMT1-1 cDNA sequence |
| 21 | ZmMT1-2 cDNA sequence |
| 22 | ZmMT2 genomic sequence |
| 23 | ZmMT2 cDNA sequence |
| 24 | ZmMT4 genomic sequence |
| 25 | ZmMT4 CDS |
| 26 | ZmMT4 amino acid sequence |
| 27 | M2L |
| 28 | M2R |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The NBS-LRR ("NLR") group of R-genes is the largest class of R-genes discovered to date. In *Arabidopsis thaliana*, over 150 are predicted to be present in the genome (Meyers, et al., (2003), Plant Cell, 15:809-834; Monosi, et al., (2004), Theoretical and Applied Genetics, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) Genome Research, 12:1871-1884; Monosi, (2004) supra; Pan, et al., (2000), Journal of Molecular Evolution, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), Current Biology: CB, 8: R226-R227). The LRR region appears to be the region that interacts with the pathogen AVR products (Michelmore, et al., (1998), Genome Res., 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), Genome Research, 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

An allele is "associated with" a trait when it is part of or linked to a DNA sequence or allele that affects the expression of the trait. The presence of the allele is an indicator of how the trait will be expressed.

As used to herein, "disease resistant" or "have resistance to a disease" refers to a plant showing increase resistance to a disease compared to a control plant. Disease resistance may manifest in fewer and/or smaller lesions, increased plant health, increased yield, increased root mass, increased plant vigor, less or no discoloration, increased growth, reduced necrotic area, or reduced wilting. In some embodiments, an allele may show resistance one or more diseases.

Disease affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; aspergillus ear and kernel rot; banded leaf and sheath spot; black bundle disease; black kernel rot; borde blanco; brown spot; black spot; stalk rot; cephalosporium kernel rot; charcoal rot; corticium ear rot; curvularia leaf spot; didymella leaf spot; diplodia ear rot and stalk rot; diplodia ear rot; seed rot; corn seedling blight; diplodia leaf spot or leaf streak; downy mildews; brown stripe downy mildew; crazy top downy mildew; green ear downy mildew; graminicola downy mildew; java downy mildew; philippine downy mildew; sorghum downy mildew; spontaneum downy mildew; sugarcane downy mildew; dry ear rot; ergot; horse's tooth; corn eyespot; fusarium ear and stalk rot; fusarium blight; seedling root rot; gibberella ear and stalk rot; gray ear rot; gray leaf spot; cercospora leaf spot; helminthosporium root rot; hormodendrum ear rot; cladosporium rot; hyalothyridium leaf spot; late wilt; northern leaf blight; white blast; crown stalk rot; corn stripe; northern leaf spot; helminthosporium ear rot; penicillium ear rot; corn blue eye; blue mold; phaeocytostroma stalk rot and root rot; phaeosphaeria leaf spot; physalospora ear rot; botryospha-eria ear rot; pyrenochaeta stalk rot and root rot; pythium root rot; pythium stalk rot; red kernel disease; rhizoctonia ear rot; sclerotial rot; rhizoctonia root rot and stalk rot; rostratum leaf spot; common corn rust; southern corn rust; tropical corn rust; sclerotium ear rot; southern blight; selenophoma leaf spot; sheath rot; shuck rot; silage mold; common smut; false smut; head smut; southern corn leaf blight and stalk rot; southern leaf spot; tar spot; trichoderma ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ring-spot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cereal mosaic.

Disease affecting plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; alternaria leaf spot; and stem rot.

Disease affecting soybean plants include, but are not limited to, alternaria leaf spot; anthracnose; black leaf blight; black root rot; brown spot; brown stem rot; charcoal rot; choanephora leaf blight; downy mildew; drechslera blight; frogeye leaf spot; leptosphaerulina leaf spot; mycoleptodiscus root rot; neocosmospora stem rot; phomopsis seed decay; phytophthora root and stem rot; phyllosticta leaf spot; phymatotrichum root rot; pod and stem blight; powdery mildew; purple seed stain; pyrenochaeta leaf spot; pythium rot; red crown rot; dactuliophora leaf spot; rhizoctonia aerial blight; rhizoctonia root and stem rot; rust; scab; sclerotinia stem rot; sclerotium blight; stem canker; stemphylium leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; alternaria black spot; anthracnose; black leg; black mold rot; black root; brown girdling root rot; cercospora leaf spot; clubroot; downy mildew; fusarium wilt; gray mold; head rot; leaf spot; light leaf spot; pod rot; powdery mildew; ring spot; root rot; sclerotinia stem rot; seed rot, damping-off; root gall smut; southern blight; verticillium wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; erwinia stalk rot and head rot; lternaria leaf blight, stem spot and head rot; botrytis head rot; charcoal rot; downy mildew; fusarium stalk rot; fusarium wilt; myrothecium leaf and stem spot; phialophora yellows; phoma black stem; phomopsis brown stem canker; phymatotrichum root rot; phytophthora stem rot; powdery mildew; pythium seedling blight and root rot; rhizoctonia seedling blight; rhizopus head rot; sunflower rust; sclerotium basal stalk and root rot; septoria leaf spot; verticillium wilt; white rust; yellow rust; dagger; pin; lesion; reniform; root knot; and chlorotic mottle; Disease affecting sorghum plants include, but are not limited to, bacterial leaf spot; bacterial leaf streak; bacterial leaf stripe; acremonium wilt; anthracnose; charcoal rot; crazy top downy mildew; damping-off and seed rot; ergot; fusarium head blight, root and stalk rot; grain storage mold; gray leaf spot; latter leaf spot; leaf blight; milo disease; oval leaf spot; pokkah boeng; pythium root rot; rough leaf spot;

rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to southern corn rust). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background. The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," *Nat Genet* 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci* USA 98:11479-11484; Thornsberry et al. (2001) "Dwarf8 polymorphisms associate with variation in flowering time," *Nat Genet* 28:286-289; reviewed by Flint-Garcia et al. (2003) "Structure of linkage disequilibrium in plants," *Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," *Annu Rev Plant Biol.* 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant co-segregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Chromosomal intervals that correlate with the disease resistance trait are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for a disease resistance trait.

Conversely, e.g., if two markers in close proximity show co-segregation with the desired phenotypic trait, it is sometimes unclear if each of those markers identify the same gene or two different gene or multiple genes. Regardless, knowledge of how many genes are in a particular physical/genomic interval is not necessary to make or practice that which is presented in the current disclosure.

The chromosome 7 interval may encompass any of the markers identified herein as being associated with the disease resistance trait comprises a sequence having at least 95% identity to SEQ ID NO: 4-10 or 13-16. Any marker located within these intervals can find use as a marker for disease resistance and can be used in the context of the methods presented herein to identify and/or select plants that have disease resistance, whether it is newly conferred or enhanced compared to a control plant. In certain embodiments, markers located upstream and downstream of ZmMM1 gene position are very tightly linked genetically and physically and hence may be used to select the ZmMM1 gene for trait introgression and products development.

Chromosomal intervals can also be defined by markers that are linked to (show linkage disequilibrium with) a disease resistant gene, and $r^2$ is a common measure of linkage disequilibrium (LD) in the context of association studies. If the $r^2$ value of LD between a chromosome 7 marker locus in an interval of interest and another chromosome 7 marker locus in close proximity is greater than ⅓ (Ardlie et al., Nature Reviews Genetics 3:299-309 (2002)), the loci are in linkage disequilibrium with one another.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) could also be used to predict disease resistance in a plant.

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) Pharmacogenomics 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants,* CABI Publishing, Wallingford. A wide range of commercially available technologies utilize these and other methods to interrogate SNPs including Masscode.™. (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than single SNPs and can be more descriptive of any particular genotype. For example, a single SNP may be allele "T" for a specific line or variety with disease resistance, but the allele 'T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the markers presented herein can readily be used as single nucleotide polymorphic (SNP) markers to select for the ZmMM1 gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the SCR disease resistance trait. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with SCRdisease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with disease resistance. For example, a SNP haplotype at the chromosome 7 QTL comprises a sequence having at least 95% identity to SEQ ID NO: 4-10 or 13-16, any SNP or indel as shown in FIG. 1, or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plants identified, modified, and/or selected by any of the methods described above are also of interest.

ZmMM1 polypeptides are encompassed by the disclosure. "ZmMM1 polypeptide" and "ZmMM1 protein" as used herein interchangeably refers to a polypeptide(s) having disease resistance activity, and is sufficiently identical to the ZmMM1 polypeptide of any one of SEQ ID NOs: 1-3. A variety of ZmMM1 polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full length sequence of a polypeptide. The term "about" when used herein in context with percent sequence identity means+/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to a ZmMM1 polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments a ZmMM1 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of any one of SEQ ID NOs: 1-3, wherein the ZmMM1 polypeptide has disease resistance when expressed in a plant.

Methods for such manipulations are generally known in the art. For example, amino acid sequence variants of a ZmMM1 polypeptide may be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of a ZmMM1 polypeptide to confer disease resistance may be improved by the use of such techniques upon the compositions of this disclosure.

Isolated or recombinant nucleic acid molecules comprising nucleic acid sequences encoding ZmMM1 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5′ and 3′ ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding ZmMM1 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding ZmMM1 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding a ZmMM1 polypeptide is a non-genomic sequence.

A variety of polynucleotides that encode ZmMM1 polypeptides or related proteins are contemplated. Such polynucleotides are useful for production of ZmMM1 polypeptides in host cells when operably linked to a suitable promoter, transcription termination and/or polyadenylation sequences. Such polynucleotides are also useful as probes for isolating homologous or substantially homologous polynucleotides that encode ZmMM1 polypeptides or related proteins.

In some embodiments the nucleic acid molecule encoding a ZmMM1 polypeptide is a polynucleotide having the sequence set forth in SEQ ID NOs: 4-10, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the ZmMM1 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding a ZmMM1 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NOs: 4-10, wherein the ZmMM1 polypeptide has disease resistance activity when expressed in a plant.

In some embodiments the nucleic acid molecule encodes a ZmMM1 polypeptide variant comprising one or more amino acid substitutions to the amino acid sequence of SEQ ID NO: 1-3.

Nucleic acid molecules that are fragments of these nucleic acid sequences encoding ZmMM1 polypeptides are also encompassed by the embodiments. "Fragment" as used herein refers to a portion of the nucleic acid sequence encoding a ZmMM1 polypeptide. A fragment of a nucleic acid sequence may encode a biologically active portion of a ZmMM1 polypeptide or it may be a fragment that can be used as a hybridization probe or PCR primer using methods disclosed below. Nucleic acid molecules that are fragments of a nucleic acid sequence encoding a ZmMM1 polypeptide comprise at least about 150, 180, 210, 240, 270, 300, 330, 360, 400, 450, or 500 contiguous nucleotides or up to the number of nucleotides present in a full-length nucleic acid sequence encoding a ZmMM1 polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the ZmMM1 polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length ZmMM1 polypeptide as set forth in SEQ ID NOs: 1-3.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a ZmMM1 polynucleotide encodes a ZmMM1 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NOs: 1-3.

The embodiments also encompass nucleic acid molecules encoding ZmMM1 polypeptide variants. "Variants" of ZmMM1 polypeptide encoding nucleic acid sequences include those sequences that encode the ZmMM1 polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the ZmMM1 polypeptides disclosed herein.

The skilled artisan will further appreciate that changes can be introduced by mutation of the nucleic acid sequences thereby leading to changes in the amino acid sequence of the encoded ZmMM1 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are generally known in the art and are disclosed in Sambrook and Russell, (2001), supra.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding a ZmMM1 polypeptide of the embodiments. In some embodiments the DNA construct comprises a polynucleotide encoding a fusion protein comprising a ZmMM1 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as E. coli or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P: 175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-V an Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENs, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an diseases resistance ZmMM1 gene allele has been identified in a genome, genome editing technologies may be used to alter or modify the polynucleotide sequence. Site specific modifications that can be introduced into the desired ZmMM1 gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the ZmMM1 polynucleotide compositions within the genome of a plant, in order to generate molecular stacks disease resistant proteins.

An "altered target site," "altered target sequence," "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. ZmMM1 Regulates Lesion-Mimic Phenotype in Maize

C117, a near-isogenic line (NIL) from a $BC_2F_7$ population derived from a single F1 cross between highland teosinte (Zea mays ssp. mexicana) and maize inbred line Mo17, with Mo17 as the recurrent parent, displays a lesion mimic phenotype. Mapping with an F2 population from C117 and Mo17, a major QTL controlling the lesion mimic phenotype was identified on chromosome 7, and it was named qLMchr7. Taking the map-based cloning approach, qLMchr7 was fine mapped into a 5 kb interval, flanked by markers M2 (SEQ ID NOs: 27 and 28) and M3 (SEQ ID NOs: 11 and 12) (FIG. 1). There is only one annotated gene within this interval based on the teosinte genome sequence, and it was named ZmMM1 (Zea mays Mexicana lesion mimic 1). Further fine mapping delimited qLMchr7 into an 1 kb interval, 950 bp downstream of the ZmMM1 CDS (FIG. 1). The 1 kb region is part of the 3'UTR of ZmMM1, as determined by 3'RACE analysis. There are a total of 20 SNPs and 7 indels between C117 and Mo17 within the 1 kb qLMchr7 region (FIG. 1). Comparing the qLMchr7 sequences of C117 with that of 46 diverse maize inbred lines identified a 30 bp specific region in C117 (SEQ ID NO: 16; and corresponding to 24 bp in Mo17, SEQ ID NO: 15) with two SNPs and one indel, of which C117 has a unique haplotype (FIG. 1).

Because qLMchr7 is part of the 3'UTR of ZmMM1, the function of qLMchr7 was tested to see if it depended on ZmMM1 and whether qLMchr7 was a regulatory element for ZmMM1 expression. While the transcript levels of ZmMM1 in Mo17 and C117 leaves were similar, the ZmMM1 protein level, as determined by western blot with an anti-ZmMM1 antibody, was higher in a NIL containing the C117 qLMchr7 allele (qLMchr7$^{c117}$) than in a NIL with the Mo17 qLMchr7 allele (qLMchr7$^{Mo17}$). This confirmed that the qLMchr7$^{c117}$ results in higher ZmMM1 protein levels than the qLMchr7$^{Mo17}$.

Transient overexpression of either the C117 or Mo17 ZmMM1 CDS with the 35S promoter in Nicotiana benthamiana caused cell death. When the 1 kb qLMchr7 fragment (SEQ ID NOs: 13 and 14) was inserted in between the ZmMM1 CDS and the terminator sequence, the ZmMM1 construct with the qLMchr7$^{c1t}$ still caused cell death in N. benthamiana, while the construct with the qLMchr7$^{Mo17}$ only induced a weak cell death phenotype. While both alleles of qLMchr7 significantly reduced the transcript and protein levels of ZmMM1 when compared with the construct without the qLMchr7 fragment, there was no difference in ZmMM1 transcript levels between the constructs with qLMchr7$^{c117}$ and qLMchr7$^{Mo17}$. However, the construct with qLMchr7$^{c117}$ resulted in higher ZmMM1 protein level than that with qLMchr7$^{Mo17}$, which is consistent with the expression results in maize. Furthermore, replacing the 24 bp specific region in qLMchr7$^{Mo17}$ with the corresponding 30 bp in C117 (resulting in qLMchr7$^{Mo17-m}$) increased the ZmMM1 protein level and resulted in a strong cell death phenotype in N. benthamiana. In contrast, replacing the 30 bp specific region in qLMchr7$^{C117}$ with the corresponding 24 bp in Mo17 (resulting in qLMchr7$^{C117-m}$) reduced the ZmMM1 protein level and resulted in a weak cell death phenotype in N. benthamiana. Thus, it was concluded that qLMchr7 regulated the expression of ZmMM1 at the protein level, and higher ZmMM1 protein level was associated with the lesion mimic phenotype in C117.

A loss-of-function ZmMM1 mutant allele was identified from a B73 EMS mutagenized population. This mutant allele (zmmm1-1) has a nonsense mutation in the $2^{nd}$ exon of ZmMM1, which introduce a premature stop codon. Overexpression of zmmm1-1 couldn't cause cell death in N. benthamiana. The zmmm1-1 mutant was crossed to a plant with the qLMchr7c$^{117}$ allele, and a pair of NILs were identified in the subsequent F3 population. Both NILs have the same qLMchr7$^{C117}$ allele (1 kb fragment). However, one has the wild type ZmMM1 from C117 (ZmMM1-qLMchr7$^{C117}$), while the other has the mutant zmmm1-1 allele (zmmm1-1-qLMchr7$^{C117}$). The ZmMM1-qLMchr7$^{C117}$ plants exhibited clear lesion mimic phenotype, but the zmmm1-1-qLMchr7$^{C117}$ plants did not. The observation confirmed that ZmMM1 is responsible for the lesion mimic phenotype in C117.

Example 2. ZmMM1 Positively Regulates Resistance Against Northern Leaf Blight (NLB), Gray Leaf Spot (GLS) and Southern Corn Rust (SCR)

The zmmm1-1 homozygous mutant plant was crossed with B73 plants to generate F1 plants and F2 populations. F2 plants with homozygous zmmm1-1 allele were significantly more susceptible to both NLB and GLS than F2 plants with the wild type ZmMM1, as determined by lesion length on infected plants in the field. The zmmm1-1 mutant F2 plants were also more susceptible to SCR than the wild type F2 plants after inoculated with P. polysora conidia in the greenhouse, as determined by fungal biomass accumulation (qRT-PCR amplification of P. polysora Actin mRNA) and visual comparison of urediospore amount. Thus, it was concluded that knocking out ZmMM1 increases susceptibility to NLB, GLS and SCR in maize.

Two pairs of NILs carrying either the qLMchr7$^{C117}$ or the qLMchr7$^{Mo17}$ allele were evaluated for their resistance to NLB, GLS and SCR in the field. The disease phenotype was rated in a 1-9 scale, with "1" being the most resistant and "9" most susceptible. NILs with the qLMchr7$^{C117}$ allele were more resistant against NLB, GLS, and SCR than NILs with the qLMchr7$^{Mo17}$ allele. The results showed that plants with the teosinte ZmMM1 allele were more resistance to multiple pathogens than plants with the maize Mo17 ZmMM1 allele.

Example 3. Identification of Target Genes for ZmMM1 Protein

ZmMM1 (CDS sequence—SEQ ID NO: 9; genomic sequence—SEQ ID NO: 5) encodes a transcription factor containing a MYB DNA binding domain (SEQ ID NO: 3). Transcriptional activity assay in protoplasts revealed that ZmMM1, when fused to the DNA binding domain (BD) of GAL4, significantly repressed the expression of the reporter gene GUS, which contained four GAL4 DNA binding site in the promoter, suggesting ZmMM1 is a transcription suppressor. DNA affinity purification sequencing (DAP-seq) was conducted and four candidate ZmMM1 target genes were identified (ZmMT1, ZmMT2, ZmMT3 and ZmMT4). ChIP-qPCR assay confirmed that ZmMM1 protein directly binds to the promoter region of the four target genes. Finally, transient expression of ZmMT3 (SEQ ID NO: 18) in *N. benthamiana* suppressed the ZmMM1-induced cell death. Since ZmMM1 positively regulates disease resistance, and negatively regulates the expression of its target genes, down-regulation in maize of ZmMT1 (SEQ ID NO: 20 and 21), ZmMT2 (SEQ ID NO: 23), ZmMT3 or ZmMT4 (SEQ ID NO: 25) enhanced the resistance to multiple pathogens. ZmMT1 (SEQ ID NO: 20 and 21), ZmMT2 (SEQ ID NO: 23), and ZmMT3 (SEQ ID NO: 18) are all long non-coding RNA (lncRNA), while ZmMT4 (SEQ ID NO: 25) encodes a polypeptide.

What is claimed:

1. A method of producing a maize plant having a heterologous gene associated with increased disease resistance, said method comprising:
   a) crossing a first maize parent plant comprising a non-endogenous maize Mexicana lesion mimic 1 (ZmMM1) polynucleotide with a second maize parent plant having susceptibility to a disease selected from the group consisting of Northern Leaf Blight (NLB), Gray Leaf Spot (GLS) and Southern Corn Rust (SCR) disease to produce a population of progeny maize plants, wherein the first maize parent plant's non-endogenous ZmMM1 polynucleotide has at least 95% identity to SEQ ID NO:4, SEQ ID NO:5, SEQ ID NO:6, SEQ ID NO:7, SEQ ID NO:8, or SEQ ID NO:9 and is not located on chromosome 7 of the first maize parent plant genome;
   b) screening the population of progeny maize plants with a selection marker located within an interval on chromosome 7 of maize plants comprising and flanked by markers M2, as set forth in primer sequences SEQ ID NOs: 27 and 28, and M3, as set forth in primer sequences SEQ ID NOs: 11 and 12; and
   c). detecting in said population at least one progeny maize plant comprising the non-endogenous ZmMM1, thereby identifying a maize plant having said heterologous gene associated with increased disease resistance.

2. The method of claim 1 wherein said non-endogenous ZmMM1 polynucleotide comprises the sequence of SEQ ID NO:4, SEQ ID NO:5, SEQ ID NO:6, SEQ ID NO:7, SEQ ID NO:8, or SEQ ID NO:9.

3. The method of claim 1 further comprising counter-selecting progeny maize plants that do not have the non-endogenous ZmMM1 polynucleotide.

4. The method of claim 1, wherein the detected progeny maize plant has increased resistance to Northern Leaf Blight (NLB) disease as compared to the second maize parent plant.

5. The method of claim 1, wherein the selected detected progeny maize plant has increased resistance to Gray Leaf Spot (GLS) disease as compared to the second parent maize plant.

6. The method of claim 1, wherein the detected progeny maize plant has increased resistance to or Southern Corn Rust (SCR) disease as compared to the second maize parent plant.

7. A method of producing a maize plant having a heterologous gene associated with increased disease resistance, said method comprising:
   a) crossing a first maize parent plant comprising a non-endogenous ZmMM1 polynucleotide with a second maize parent plant having susceptibility to a disease selected from the group consisting of Northern Leaf Blight (NLB), Gray Leaf Spot (GLS) and Southern Corn Rust (SCR) disease to produce a population of progeny maize plants, wherein the first maize parent plant's non-endogenous ZmMM1 polynucleotide is not located on chromosome 7 of the first maize parent plant genome and comprises a polynucleotide encoding a polypeptide having an amino acid sequence that is at least 90% identical to SEQ ID NO:1, SEQ ID NO:2, or SEQ ID NO:3;
   b) screening the population of progeny maize plants to identify one or more progeny maize plants having the non-endogenous ZmMM1 polynucleotide sequence; and
   c) detecting in said population at least one progeny maize plant comprising the non-endogenous ZmMM1 a polynucleotide, thereby identifying a maize plant having said heterologous gene associated with increased disease resistance.

8. The method of claim 7 wherein said non-endogenous ZmMM1 polynucleotide encodes a polypeptide having an amino acid sequence SEQ ID NO:1, SEQ ID NO:2, or SEQ ID NO:3.

9. The method of claim 7 further comprising counter-selecting progeny maize plants that do not have the non-endogenous ZmMM1 polynucleotide.

10. The method of claim 7, wherein the detected progeny maize plant has increased resistance to Northern Leaf Blight (NLB) disease as compared to the second maize parent plant.

11. The method of claim 7, wherein the detected progeny maize plant has increased resistance to Gray Leaf Spot (GLS) disease as compared to the second maize parent plant.

12. The method of claim 7, wherein the detected progeny maize plant has increased resistance to Northern Leaf Blight (NLB) disease as compared to the second maize parent plant.

13. A method of detecting a progeny maize plant comprising a heterologous gene, said method comprising:
   a) crossing a first maize parent plant comprising a non-endogenous ZmMM1 polynucleotide with a second maize parent plant having susceptibility to a disease selected from the group consisting of Northern Leaf Blight (NLB), Gray Leaf Spot (GLS) and Southern Corn Rust (SCR) disease to produce a population of progeny maize plants, wherein the first maize parent plant's non-endogenous ZmMM1 polynucleotide is not located on chromosome 7 of the first maize plant genome, further wherein said non-endogenous ZmMM1 polynucleotide encodes a polypeptide having an amino acid sequence that is at least 95% identical to SEQ ID NO:1, SEQ ID NO:2, or SEQ ID NO:3;
   b) detecting progeny maize plants comprising said the non-endogenous ZmMM1 polynucleotide sequence, by contacting nucleic acids recovered from said progeny maize plants with a selection marker located within an interval on chromosome 7 of maize plants comprising and flanked by markers M2, as set forth in primer sequences SEQ ID NOs: 27 and 28, and M3, as set forth in primer sequences SEQ ID NOs: 11 and 12.

14. The method of claim 13 wherein said non-endogenous ZmMM1 polynucleotide encodes a polypeptide having an amino acid sequence SEQ ID NO:1, SEQ ID NO:2, or SEQ ID NO:3.

* * * * *